(12) United States Patent
King et al.

(10) Patent No.: US 9,724,395 B2
(45) Date of Patent: Aug. 8, 2017

(54) TREATMENT OF CANCER WITH IMMUNE STIMULATORS

(71) Applicant: SciClone Pharmaceuticals, Inc., Foster City, CA (US)

(72) Inventors: Robert S. King, Fremont, CA (US); Cynthia W. Tuthill, Hercules, CA (US); Friedhelm Blobel, Foster City, CA (US)

(73) Assignee: SciClone Pharmaceuticals, Inc., Foster City, CA (US)

(*) Notice: Subject to any disclaimer, the term of this patent is extended or adjusted under 35 U.S.C. 154(b) by 0 days.

(21) Appl. No.: 14/918,675

(22) Filed: Oct. 21, 2015

(65) Prior Publication Data

US 2016/0106812 A1    Apr. 21, 2016

Related U.S. Application Data

(60) Provisional application No. 62/066,862, filed on Oct. 21, 2014, provisional application No. 62/215,433, filed on Sep. 8, 2015.

(51) Int. Cl.

| | | |
|---|---|---|
| *A61K 38/22* | (2006.01) |
| *A61K 39/395* | (2006.01) |
| *A61K 45/06* | (2006.01) |
| *A61K 31/44* | (2006.01) |
| *A61K 31/165* | (2006.01) |
| *C07K 16/28* | (2006.01) |
| *A61K 31/655* | (2006.01) |
| *A61K 38/19* | (2006.01) |
| *A61K 38/20* | (2006.01) |
| *A61K 38/21* | (2006.01) |

(52) U.S. Cl.
CPC ........ *A61K 38/2292* (2013.01); *A61K 31/165* (2013.01); *A61K 31/44* (2013.01); *A61K 31/655* (2013.01); *A61K 38/193* (2013.01); *A61K 38/2046* (2013.01); *A61K 38/21* (2013.01); *A61K 39/39558* (2013.01); *A61K 45/06* (2013.01); *C07K 16/2818* (2013.01); *C07K 2317/70* (2013.01)

(58) Field of Classification Search
None
See application file for complete search history.

(56) References Cited

U.S. PATENT DOCUMENTS

| | | | | |
|---|---|---|---|---|
| 2005/0049191 A1* | 3/2005 | Rudolph | ............ | A61K 38/2292 424/192.1 |
| 2008/0300166 A1* | 12/2008 | Tuthill | ............... | A61K 38/2292 514/1.1 |
| 2010/0092499 A1* | 4/2010 | Moviglia | ........... | A61K 39/0011 424/185.1 |

FOREIGN PATENT DOCUMENTS

| | | | | |
|---|---|---|---|---|
| WO | WO 2006/062917 A2 | 6/2006 | | |
| WO | WO 2009/075813 A1 | 6/2009 | | |
| WO | WO 2009/076587 A1 | 6/2009 | | |
| WO | WO 2009/079338 A1 | 6/2009 | | |
| WO | WO2009079338 | * | 6/2009 | ............ A61K 38/00 |
| WO | PCT/US2013/057542 | * | 3/2014 | ............ A61K 39/00 |

OTHER PUBLICATIONS

Mangana et al., Sorafenib in melanoma, Exp. Opin. Investig. Drugs, 21, 557-568, 2012.*
Meisel et al., "Granulocyte-Macrophage Colony-stimulating Factor to Reverse Sepsis-associated Immunosuppression" *American Journal of Respiratory and Critical Care Medicine*, 180(7): 640-648.
International Search Report based on International Patent Application No. PCT/US2015/056609, mailed on Mar. 4, 2016.
Written Opinion based on International Patent Application No. PCT/US2015/056609, mailed on Mar. 4, 2016.

* cited by examiner

*Primary Examiner* — Ellly-Gerald Stoica
(74) *Attorney, Agent, or Firm* — Cooley LLP

(57) ABSTRACT

The present invention provides compositions and methods for treating cancer or a metastasis thereof in a subject. In some embodiments, the methods involve administering a composition comprising therapeutically effective amount of at least one immune stimulator to the subject. In some embodiments, a combination of at least two immune stimulators is used for the treatment. In some embodiments, the combination includes an alpha thymosin peptide and an additional immune stimulator, and/or optionally one or more additional anti-cancer agents.

25 Claims, 22 Drawing Sheets

Lung Metastasis Foci in the Different Groups at Day 13 post Tumor Inoculation

Note: No lung metastasis was found in Cyclophsphomide treatment group.

SEQUENCE LISTING

```
<160> NUMBER OF SEQ ID NOS: 1

<210> SEQ ID NO 1
<211> LENGTH: 28
<212> TYPE: PRT
<213> ORGANISM: Artificial Sequence
<220> FEATURE:
<223> OTHER INFORMATION: Thymosin Alpha 1 Peptide

<400> SEQUENCE: 1

Ser Asp Ala Ala Val Asp Thr Ser Ser Glu Ile Thr Thr Lys Asp Leu
1               5                   10                  15

Lys Glu Lys Lys Glu Val Val Glu Glu Ala Glu Asn
            20                  25
```

TREATMENT OF CANCER WITH IMMUNE STIMULATORS

CROSS-REFERENCE TO RELATED APPLICATIONS

This application claims priority to, and the benefit of U.S. Provisional Patent Application Ser. No. 62/066,862, filed on Oct. 21, 2014 and U.S. Provisional Patent Application Ser. No. 62/215,433, filed on Sep. 8, 2015, each of which is incorporated by reference for all purposes.

FIELD OF THE INVENTION

The present invention relates to compositions and methods for treating cancer, such as melanoma, or metastases thereof.

BACKGROUND OF THE INVENTION

Many drugs or drug candidates have been developed for the treatment of various cancers, including some small molecule compounds. However, current treatments for many cancers are not very effective in patients with specific subsets of cancers, or are too toxic in such patients or in general.

Skin cancer is the most common form of cancer in the United States. In 2007, The American Cancer Society estimates that approximately 8,110 deaths will occur from melanoma and another 59,940 cases of melanoma are expected to be diagnosed in this country.

Melanoma is a malignant tumor of melanocytes which are found predominantly in skin but also in bowel and the eye (uveal melanoma). It is one of the rarer types of skin cancer but causes the majority of skin cancer related deaths.

The currently available treatment includes surgical removal of the tumor; adjuvant treatment; chemo- and immunotherapy, or radiation therapy. Of particular danger are metastases of the primary melanoma tumor. However, there remains a need in the art for improved treatments of melanoma.

SUMMARY OF THE INVENTION

The present invention provides compositions and methods of treating a cancer or combination of cancers in a subject. In some embodiments, the subject is a mammal. In some embodiments, the mammal is a human.

In some embodiments, the methods comprise administering a composition comprising therapeutically effective amount of a first immune stimulator and a second immune stimulator to the subject. In some embodiments, the first immune stimulator is an alpha thymosin peptide. In some embodiments, the second immune stimulator is a compound other than IL-2, interferon-α, or IRX-2. In some embodiments, the second immune stimulator comprises a specific immunostimulant. In some embodiment, the second immune stimulator comprises a non-specific immunostimulant.

In some embodiment, the second immune stimulator is an immunostimulant that is effective in treating sepsis. In some embodiment, the immunostimulant comprises granulocyte macrophage colony stimulating factor (GM-CSF), programmed cell death-1 (PD-1) inhibitors and/or interleukin-7 (IL-7).

In some embodiment, the composition further comprises an additional anti-cancer agent. In some embodiments, the additional anti-cancer agent is a chemotherapeutic agent.

In some embodiment, the second immune stimulator is administered to said subject at a dosage of about 0.01-1000 mg/day.

In some embodiment, the second immune stimulator comprises GM-CSF, and the dosage of GM-CSF is about 10 to 500 mcg/m$^2$, such as about 125 to about 250 10 to 500 mcg/m$^2$.

In some embodiment, the second immune stimulator comprises a PD-1 inhibitor. In some embodiments, the PD-1 inhibitor is an agent that inhibits PD-1, such as an antibody against PD-1. In some embodiments, the PD-1 inhibitor is an agent that inhibits the ligand for PD-1, such as an antibody against the ligand for PD-1. In some embodiment, the dosage of the PD-1 inhibitor is about 0.1 to 10 mg/kg, such as about 1-5 mg/kg, or about 2-3 mg/kg. In some embodiments, the PD-1 inhibitor is an anti-PD-L1 antibody, and the dosage is about 15-20 mg/kg. In some embodiments, the anti-PD-L1 antibody is used at a 1200 mg flat dose every two, three, or four weeks.

In some embodiments, the second immune stimulator comprises an interleukin that is not IL-2. In some embodiments, the interleukin is IL-7. In some embodiment, the dosage of IL-7 is about 0.1 to 100 mcg/kg, such as about 1 to 50 mcg/kg, or about 3 to 30 mcg/kg.

In some embodiments, the alpha thymosin peptide is administered to the subject during at least a portion of the treatment at a dosage within a range of about 0.1 to 100 mg/day, such as about 0.5-50 mg/day, or about 0.1-10 mg/day.

In some embodiments, the alpha thymosin peptide is thymosin alpha 1 (TA1).

In some embodiments, the methods comprise administration of TA1 daily for a period of about 1-10 days, followed by about 1-5 days of non-administration of TA1. In some embodiments, TA1 is administered daily for about 3-5 days, followed by about 2-4 days of non-administration of TA1. In some embodiments, TA1 is administered daily for about 4 days, followed by about 3 day's non-administration of TA1.

In some embodiments, the methods further comprise administering a kinase inhibitor. In some embodiments, the kinase inhibitor comprises sorafenib. In some embodiments, the kinase inhibitor is administered to said patient at a dosage within a range of about 10-200 mg/kg/day.

In some embodiments, the methods further comprise administering an antineoplastic heat shock apoptosis activator (HSAA). In some embodiments, the HSAA comprises STA-4783 (elesclomol). In some embodiments, the HSAA is administered to said patient at a dosage within a range of about 0.01-100 mg/kg/day.

In some embodiments, the methods further comprise administering an inhibitor of cytotoxic T lymphocyte-associated antigen 4 (CTLA4), such as an antibody against CTLA4. In some embodiments, the CTLA4 antibody comprises 9H10, MDC010, 1F4, BNI3, Q01, A01, M08, 1B8, WKH203, ab9984, ab13486, ipilimumab, ticilimumab or a combination thereof. In some embodiments, the CTLA4 antibody is administered to said patient at a dosage within a range of about 0.001-50 mg/kg/day.

In some embodiments, the methods further comprise administering an alkylating antineoplastic agent (AlkAA). In some embodiments, the alkylating antineoplastic agent (AlkAA) comprises dacarbazine (DTIC). In some embodiments, the alkylating antineoplastic agent (AlkAA) is administered to said patient at a dosage within a range of about 700-1300 mg/kg/day.

In some embodiments, the methods further comprise administering a chemotherapeutic agent to the subject. In some embodiments, the chemotherapeutic agent is dacarbazine (DTIC) or cisplatin.

In some embodiments, the cancer is melanoma.

The present invention also provides methods of treating cancer or a metastasis thereof in a subject comprising administering a composition comprising therapeutically effective amount of an immune stimulator, wherein the immune stimulator is effective in treating sepsis. In some embodiments, the cancer is melanoma. In some embodiments, the subject is a mammal. In some embodiments, the mammal is a human. In some embodiments, the immunostimulant that is effective in treating sepsis comprises granulocyte macrophage colony stimulating factor (GM-CSF), programmed cell death-1 (PD-1) inhibitors and/or interleukin-7 (IL-7), or any combination thereof.

In some embodiments, the composition further comprises an additional anti-cancer agent. In some embodiments, the additional anti-cancer agent is an alpha thymosin peptide. In some embodiments, the alpha thymosin peptide is thymosin alpha 1 (TA1).

In some embodiments, the method further comprises administering a chemotherapeutic agent to the subject. In some embodiments, the chemotherapeutic agent is dacarbazine (DTIC) or cisplatin.

The present invention also provides methods for determining the responsiveness of a human subject to cancer treatment. In some embodiments, the cancer is melanoma. In some embodiments, the methods comprise determining the level of activity of one or more biomarkers in a biological sample from a human subject. In some embodiments, the biomarkers are selected from the group consisting of IL-1β, IL-4, IL-6, and IL-10. In some embodiments, the cancer treatment is according to the methods described herein.

In some embodiments, a higher than normal level of IL-1β activity is indicative that the human subject is responsive to the treatment.

In some embodiments, a lower than normal level of IL-4 activity is indicative that the human subject is responsive to the treatment.

In some embodiments, a higher than normal level of IL-6 activity is indicative that the human subject is responsive to the treatment.

In some embodiments, a higher than normal level of IL-10 activity is indicative that the human subject is responsive to the treatment.

The present invention also provides methods for determining dosage or regimen for the treatment of cancer in a human subject. In some embodiments, the cancer is melanoma. In some embodiments, the methods comprise determining the level of activity of one or more biomarkers in a biological sample from a human subject being treated. In some embodiments, the biomarkers are selected from the group consisting of IL-1β, IL-4, IL-6, and IL-10.

In some embodiments, a decreased level of IL-1β activity after the treatment is indicative that the treatment is effective. In some embodiments, an unchanged or increased level of IL-1β activity after the treatment is indicative that the treatment is not effective. The dosage or regimen of the treatment can be modified accordingly.

In some embodiments, an increased level of IL-4 activity after the treatment is indicative that the human subject is responsive to the treatment. In some embodiments, an unchanged or decreased level of IL-4 activity after the treatment is indicative that the treatment is not effective. The dosage or regimen of the treatment can be modified accordingly.

In some embodiments, a decreased level of IL-6 activity after the treatment is indicative that the treatment is effective. In some embodiments, an unchanged or increased level of IL-6 activity after the treatment is indicative that the treatment is not effective. The dosage or regimen of the treatment can be modified accordingly.

In some embodiments, a decreased level of IL-10 activity after the treatment is indicative that the treatment is effective. In some embodiments, an unchanged or increased level of IL-10 activity after the treatment is indicative that the treatment is not effective. The dosage or regimen of the treatment can be modified accordingly.

DETAILED DESCRIPTION

Figure 1A:
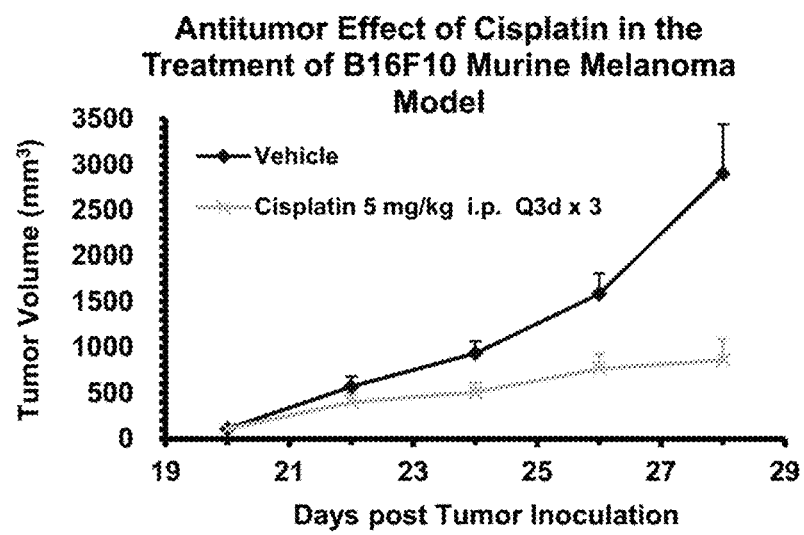
FIG. 1A depicts antitumor effect of cisplatin in treatment of B16F10 murine melanoma model as indicated by tumor volume post tumor inoculation.

The present invention is directed to methods of treating and/or preventing cancer in a subject. In some embodiments, the cancer is melanoma or metastases thereof. In some embodiments, the methods involve administering a composition comprising at least one immune stimulator to the subject.

In some embodiments, methods of the present invention can be applied in the treatment of early stage cancers including early neoplasias that may be small, slow growing, localized and/or nonaggressive, for example, with the intent of curing the disease or causing regression of the cancer, as well as in the treatment of intermediate stage and in the treatment of late stage cancers including advanced and/or metastatic and/or aggressive neoplasias, for example, to slow the progression of the disease, to reduce metastasis or to increase the survival of the patient. Similarly, the combinations may be used in the treatment of low grade cancers, intermediate grade cancers and or high grade cancers.

In some embodiments, methods of the present invention can also be used in the treatment of indolent cancers, recurrent cancers including locally recurrent, distantly recurrent and/or refractory cancers (i.e. cancers that have not responded to treatment), metastatic cancers, locally advanced cancers and aggressive cancers. Thus, an "advanced" cancer includes locally advanced cancer and metastatic cancer and refers to overt disease in a patient, wherein such overt disease is not amenable to cure by local modalities of treatment, such as surgery or radiotherapy. The term "metastatic cancer" refers to cancer that has spread from one part of the body to another. Advanced cancers may also be unresectable, that is, they have spread to surrounding tissue and cannot be surgically removed.

In some embodiments, methods of the present invention can also be used in the treatment of drug resistant cancers, including multidrug resistant tumors. As is known in the art, the resistance of cancer cells to chemotherapy is one of the central problems in the management of cancer.

One skilled in the art will appreciate that many of these categories may overlap, for example, aggressive cancers are typically also metastatic. "Aggressive cancer," as used herein, refers to a rapidly growing cancer. One skilled in the art will appreciate that for some cancers, such as breast cancer or prostate cancer the term "aggressive cancer" will refer to an advanced cancer that has relapsed within approximately the earlier two-thirds of the spectrum of relapse times for a given cancer, whereas for other types of cancer, nearly all cases present rapidly growing cancers which are considered to be aggressive. The term can thus cover a subsection of a certain cancer type or it may encompass all of other cancer types.

In some embodiments, cancers to be treated by the methods of the present invention in include, but are not limited to, AIDS-related cancers, adrenocortical cancer, anal cancer, bladder cancer, bowel cancer, brain and central nervous system cancers, breast cancer, carcinoid cancers, cervical cancer, chondrosarcoma, choriocarcinoma, colorectal cancer, endocrine cancers, endometrial cancer, Ewing's sarcoma, eye cancer, gastric cancer, gastrointestinal cancer, genitourinary cancers, glioma, gynecological cancer, head and neck cancer, hepatocellular cancer, Hodgkin's disease, hypopharyngeal cancer, islet cell cancer, Kaposi's sarcoma, kidney cancer, laryngeal cancer, leukemia, liver cancer, lung cancer (e.g., Non-Small Cell Lung Cancer), lymphoma, melanoma, basal cell carcinoma, mesothelioma, myeloma, nasopharyngeal cancer, neuroblastoma, non-Hodgkin's lymphoma, esophagael cancer, osteosarcoma, ovarian cancer, pancreatic cancer, pituitary cancer, renal cell carcinoma, prostate cancer, retinoblastoma, rhabdomyosarcoma, sarcoma, skin cancer, squamous cell carcinoma, stomach cancer, testicular cancer, thymus cancer, thyroid cancer, transitional cell cancer, trophoblastic cancer, uterine cancer, vaginal cancer, Waldenstrom's macroglobulinemia, Wilm's cancer, and leukemia.

According to the methods of the present invention, the term "subject," and variants thereof as used herein, includes any subject that has, is suspected of having, or is at risk for having a disease or condition. Suitable subjects (or patients) include mammals, such as laboratory animals (e.g., mouse, rat, rabbit, guinea pig), farm animals, and domestic animals or pets (e.g., cat, dog). Non-human primates and, preferably, human patients, are included. A subject "at risk" may or may not have detectable disease, and may or may not have displayed detectable disease prior to the diagnostic or treatment methods described herein. "At risk" denotes that a subject has one or more so-called risk factors, which are measurable parameters that correlate with development of a condition described herein, which are described herein. A subject having one or more of these risk factors has a higher probability of developing a condition described herein than a subject without these risk factor(s). In some embodiments, the subject is a mammal. In some embodiments, the subject is a human. In some embodiments, the subject is a human diagnosed as having melanoma. In some embodiments, the subject is a human suspected to have melanoma. In some embodiments, the subject is a human having high risk of developing melanoma. In some embodiments, the subject is a melanoma patient with metastasis. In some embodiments, the subject is a melanoma patient with high risk of metastasis.

In some embodiments, methods of the present invention are used in the treatment of melanoma. In some embodiments, the melanoma is one of lentigo maligna, lentigo maligna melanoma, superficial spreading melanoma, acral lentiginous melanoma, mucosal melanoma, nodular melanoma, polypoid melanoma, desmoplastic melanoma, amelanotic melanoma, soft-tissue melanoma, melanoma with small nevus-like cells, melanoma with features of a Spitz nevus, uveal melanoma, or combinations thereof.

In some embodiments, the human patient has a melanoma at Stage 0, I, II, III or IV, or their respective subdivisions. In certain embodiments, the melanoma being treated is malignant metastatic melanoma. In certain embodiments, the melanoma being treated is stage I, stage II, stage III or stage IV. In other embodiments, the melanoma being treated is stage M1a, M1b or M1c melanoma. For detailed staging information, see Balch et al. (2001, "Final version of the American Joint Committee on Cancer staging system for cutaneous melanoma". J Clin Oncol 19 (16): 3635-48. PMID 11504745), which is incorporated by reference in its entirety.

In some embodiments, the human patient has one or more early signs of melanoma, such as changes to the shape or color of existing moles, including but not limited to, asymmetry, irregular borders, variegated color, greater than about 6 mm in diameter, evolving over time, itch, ulcerate or bleed. In some embodiments, the human patient has nodular melanoma, and early signs include, but are not limited to, the appearance of a new lump anywhere on the skin, elevated above the skin surface, firm to the touch, and continuous growth.

Metastasis, or metastatic disease, is the spread of a cancer from one organ to another. Some cancer cells acquire the ability to penetrate the walls of lymphatic and/or blood vessels, after which they are able to circulate through the bloodstream to other sites and tissues in the body. After the tumor cells come to rest at another site, they re-penetrate the vessel or walls and continue to multiply, eventually forming another clinically detectable tumor.

In some embodiments, the melanoma is malignant metastatic melanoma. In some embodiments, metastatic melanoma causes nonspecific paraneoplastic symptoms in the patient, including but not limited to, loss of appetite, nausea, vomiting and fatigue. In some embodiments, the patient has brain metastases. In some embodiments, the melanoma spread to the liver, bones, abdomen and/or distant lymph nodes.

In some embodiments, the subject to be treated has high risk of developing melanoma. In some embodiments, the human subject is a Caucasian. In some embodiments, the human patient is living in sunny climates with extensive exposure to UV light. In some embodiments, the subject to be treated has one or more genetic mutations that increase one's susceptibility to melanoma. In some embodiments, the genetic mutations are in the BRAF, MC1R, CDKN2A, CDK4, nucleotide excision repair (NER) enzymes (a.k.a. xeroderma pigmentosum, XP), multiple tumor suppressor 1 (MTS1), and/or MDM2.

Methods for diagnosis of melanoma are well known, such as those described in Wurmand Soyer (October 2010, "Scanning for melanoma". Australian Prescriber (33): 150-5), which is incorporated by reference in its entirety. In some embodiments, the diagnosis is by virtual examination. In some embodiments, the diagnosis is by X-rays, CT scans, MRIs, PET and PET/CTs, ultrasound, LDH testing and/or photoacoustic detection.

After melanoma has been diagnosed, further tests can be used to determine if cancer cells have spread within the skin or to other parts of the body. Tests include but are not limited to, physical exam and history, lymph node mapping and sentinel lymph node biopsy, CT scan, PET scan, MRI, and blood chemistry studies.

The terms "treating" and "treatment" as used herein refer to an approach for obtaining beneficial or desired results including clinical results, and may include even minimal changes or improvements in one or more measurable markers of the disease or condition being treated. A treatment is usually effective to reduce at least one symptom of a condition, disease, disorder, injury or damage. Exemplary markers of clinical improvement will be apparent to persons skilled in the art. Examples include, but are not limited to, one or more of the following: decreasing the severity and/or frequency one or more symptoms resulting from the disease, diminishing the extent of the disease, stabilizing the disease (e.g., preventing or delaying the worsening of the disease), delay or slowing the progression of the disease, ameliorating the disease state, decreasing the dose of one or more other medications required to treat the disease, and/or increasing the quality of life, etc.

"Prophylaxis," "prophylactic treatment," or "preventive treatment" refers to preventing or reducing the occurrence or severity of one or more symptoms and/or their underlying cause, for example, prevention of a disease or condition in a subject susceptible to developing a disease or condition (e.g., at a higher risk, as a result of genetic predisposition, environmental factors, predisposing diseases or disorders, or the like).

In some embodiments, the methods comprise administering therapeutically effective amount and/or prophylactically effective amount of a composition comprising at least one immunostimulant to the subject. The term "therapeutically effective amount" as used herein, refers to the level or amount of one or more agents needed to treat a condition, or reduce or prevent injury or damage, optionally without causing significant negative or adverse side effects. A "prophylactically effective amount" refers to an amount of an agent sufficient to prevent or reduce severity of a future disease or condition when administered to a subject who is susceptible and/or who may develop a disease or condition.

Immune stimulators, a.k.a. immunostimulants, or immunostimulators, refer to substances that stimulate the immune system. In some embodiments, the immune stimulators of the present invention can induce activation or increase activity of one or more positive regulators of the immune system. In some embodiments, the immune stimulators of the present invention can induce deactivation or decrease activity of one or more negative regulators of the immune system. As used herein, the term activity refers to the activity of a given target at the genomic DNA level, transcriptional level, post-transcriptional level, translational level, post-translational level, including but not limited to, gene copy number, mRNA transcription rate, mRNA abundance, mRNA stability, protein translation rate, protein stability, protein modification, protein activity, protein complex activity, etc. In some embodiments, an immune stimulator can be a specific immunostimulant. Specific immunositmulants are substances that provide antigenic specificity in immune response, such as vaccines or antigens. In some embodiments, an immune stimulator can be a non-specific immunostimulant. Non-specific immunositmulants act irrespective of antigenic specificity to augment immune response of other antigen or stimulate components of the immune system without antigenic specificity, such as adjuvants. An immune stimulator to be used in the methods of the present invention can be recombinant, synthetic, natural preparations, or combinations thereof.

In some embodiments, at least one immunostimulant is effective in treating sepsis.

In some embodiments, at least one immunostimulant is a thymosin peptide (thymosins). Thymosins are small proteins and are present in many animal tissues. Thymosins were originally isolated from the thymus, but most are now known to be present in many other tissues. As used herein, thymosins include thymosin α, thymosin β, thymosin γ, and functional variants thereof. In certain embodiments, the thymosin is thymosin alpha (or alpha thymosin). In certain embodiments, the thymosin is prothymosin alpha (PTMA). In certain embodiments, the thymosin is thymosin alpha 1 ("TA1", a.k.a. Thymosin alpha-1, Thymosin a-1, Thymosin α-1, or alpha thymosin) and functional variants having structural homology to TA1. In some embodiments, TA1 is a peptide having the amino acid sequence (N-acetyl)-Ser-Asp-Ala-Ala-Val-Asp-Thr-Ser-Ser-Glu-Ile-Thr-Thr-Lys-Asp-Leu-Lys-Glu-Lys-Lys-Glu-Val-Val-Glu-Glu-Ala-Glu-Asn-OH (SEQ ID NO: 1). The amino acid sequence of TA1 is disclosed in U.S. Pat. No. 4,079,137, the disclosure of which is hereby incorporated by reference. TA1 is a non-glycosylated 28-amino acid peptide having an acetylated N-terminus, and a molecular weight of about 3108. In some embodiments, a synthetic version of TA1 is used. In some embodiments, the synthetic version of TA1 is commercially available in certain countries under the trade name ZADAXIN (thymalfasin). As used herein, the term TA1 also refers to functional variants or fragments derived from SEQ ID NO: 1.

In some embodiments, at least one immune stimulator is thymosin alpha 1 (TA1). Alpha thymosin peptides comprise thymosin alpha 1 (TA1) peptides including naturally occurring TA1 as well as synthetic TA1 or recombinant TA1 having the amino acid sequence of naturally occurring TA1, amino acid sequences substantially similar thereto, or an abbreviated sequence form thereof, and their biologically active analogs having substituted, deleted, elongated, replaced, or otherwise modified sequences which possess bioactivity substantially similar to that of TA1, e.g., a TA1 derived peptide having sufficient amino acid homology with TA1 such that it functions in substantially the same way with substantially the same activity as TA1. Suitable dosages of the alpha thymosin peptide can be within the range of about 0.001-10 mg/kg/day. In some embodiments, TA1 has the amino acid sequence disclosed in U.S. Pat. No. 4,079,137, the disclosure of which is incorporated herein by reference. TA1 initially isolated from Thymosin Fraction 5 (TF5) has been sequenced and chemically synthesized. TA1 is a 28 amino acid peptide with a molecular weight of 3108.

In some embodiments, effective amounts of an alpha thymosin peptide are amounts which may be dosage units within a range corresponding to about 0.01-20 mg of TA1, about 1-10 mg of TA1, about 2-10 mg of TA1, about 2-7 mg of TA1, or about 3-6.5 mg of TA1, and may comprise about 1.6, 3.2 or 6.4 mg of TA1, or about 3.2 or 6.4 mg of TA1. A dosage unit may be administered once per day, or a plurality of times per day. In some embodiments, TA1 is administered to a subject at a dosage within a range of about 0.5-10 mg/day. In certain embodiments, the TA1 dosage is within a range of about 1.5-7 mg/day, or within a range of about 1.6-6.4 mg/day. In certain embodiments, the TA1 dosage is within a range of about 1.7-10 mg/day, about 1.7-7 mg/day, or about 3-7 mg/day. In some embodiments, the effective dosages include about 1.6, 3.2 or 6.4 mg/day. In some embodiments, TA1 is administered to a subject at a dosage of about 0.01 to about 6 mg/kg. In some embodiments, TA1 is administered to a subject once a day, twice a day, three times a day, four times a day, or more. In some embodiments, TA1 is administered to a subject alone or with one or more additional immune stimulators.

TA1 peptides include naturally occurring TA1 as well as synthetic TA1 or recombinant TA1 having the amino acid sequence of naturally occurring TA1, amino acid sequences substantially similar thereto, or an abbreviated sequence form thereof, and their biologically active analogs having substituted, deleted, elongated, replaced, or otherwise modified sequences which possess bioactivity substantially similar to that of TA1, e.g., a TA1 derived peptide having sufficient amino acid homology with TA1 such that it functions in substantially the same way with substantially the same activity as TA1. In some embodiments, suitable dosages of the thymosin can be within the range of about 0.001-10 mg/kg/day, such as 0.001, 0.005, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 2.0, 3.0, 4.0, 5.0, 6.0, 7.0, 8.0, 9.0, 10.0, or more mg/kg/day. In some embodiments, TA1 has the amino acid sequence disclosed in U.S. Pat. No. 4,079,137, the disclosure of which is incorporated herein by reference.

TA1 initially isolated from Thymosin Fraction 5 (TF5) has been sequenced and chemically synthesized. TA1 is a 28 amino acid peptide with a molecular weight of 3108. The term TA1 also includes functional variants and functional fragment of TA1, naturally occurring, synthetic or recombinant thymosin. TA1 was originally isolated from bovine thymus, where it was shown to reconstitute "immune function" in thymectomized animal models. In some embodiments, the thymosin comprises the amino acid sequence of SEQ ID NO:1 (where an acylated, e.g., acetylated, N-terminus is optional). In some embodiments, the thymosin comprises an amino acid sequence that is substantially similar to TA1, and maintains the immunomodulatory activity of TA1. The substantially similar sequence may have, for example, from about 1 to about 10 amino acid deletions, insertions, and/or substitutions (collectively) with respect to TA1. For example, the thymosin may have from about 1 to about 5 (e.g., 1, 2, or 3) amino acid insertions, deletions, and/or substitutions (collectively) with respect to TA1.

Thus, the thymosin may comprise an abbreviated TA1 sequence, for example, having deletions of from 1 to about 10 amino acids, or from about 1 to 5 amino acids, or 1, 2 or 3 amino acids with respect to TA1. Such deletions may be at the N- or C-terminus, and/or internal, so long as the immunomodulatory activity of the peptide is substantially maintained. Alternatively, or in addition, the substantially similar sequence may have from about 1 to about 5 amino acid insertions (e.g., 1, 2, or 3 amino acid insertions) with respect to TA1, where the immunomodulatory activity of TA1 is substantially maintained. Alternatively, or in addition, the substantially similar sequence may have from 1 to about 10 amino acid substitutions, where the immunomodulatory activity is substantially maintained. For example, the substantially similar sequence may have from 1 to about 5, or 1, 2, or 3 amino acid substitutions, which may include conservative and non-conservative substitutions. In some embodiments, the substitutions are conservative. Generally, conservative substitutions include substitutions of a chemically similar amino acid (e.g., polar, non-polar, or charged). Substituted amino acids may be selected from the standard 20 amino acids or may be a non-standard amino acid (e.g., a conserved non-standard amino acid).

In some embodiments, the thymosin comprises an amino acid sequence having at least 70% sequence identity to SEQ ID NO:1, while maintaining the immunomodulatory activity of TA1. For example, the thymosin may comprise an amino acid sequence having at least 80%, 85%, 90%, 95% sequence identity to SEQ ID NO:1. The thymosin may comprise an amino acid sequence having 100% sequence identity to SEQ ID NO:1. In some embodiments, the N-terminus may be optionally acylated (e.g., acetylated) or alkylated, for example, with a C1-10 or C1-C7 acyl or alkyl group.

In certain embodiments, the substantially similar and homologous peptides described above may function at a level of at least about 50%, 70%, 80%, 90%, or about 100% relative to TA1 (SEQ ID NO:1).

The thymosin may be prepared synthetically, for example, by solid phase synthesis, or may be made recombinantly and purified by known techniques. The thymosin may also be provided in lyophilized form, and reconstituted with sterile (e.g., aqueous) diluent prior to administration. Formulations of thymosin may be administered by subcutaneous injection, or other effective route.

In certain embodiments, the thymosin is pegylated to increase its half-life in circulation. Such strategies for increasing the half-life of therapeutic proteins are well known.

Thymosin is thought to play a role in inflammatory and innate immune responses, and to facilitate discrimination of self from non-self in mammals. Activation of PAMP (pathogen-associated molecular patterns) ligands by thymosin leads to stimulation of intracellular signal transduction pathways resulting in expression of co-stimulatory molecules, pro-inflammatory cytokines, nitric oxide, and eicosanoids. Thymosin may affect, for example, dendritic cells, T cells, B cells, and NK cells.

In some embodiments, TA1 is combined with a second immune stimulator.

In some embodiments, the second immune stimulator is an immune stimulator that is effective in treating sepsis. In some embodiments, the second immune stimulator is GM-CSF, interferon (e.g., interferon-γ), interleukin 7, interleukin 15, or an inhibitor of PD-1. In some embodiments, the immune stimulator that is effective in treating sepsis is capable of reducing T-cell exhaustion in the subject. In some embodiments, the immune stimulator is a substance capable of increasing the activity of GM-CSF, interferon (e.g., interferon-γ), or interleukin 7 or interleukin 15, see Boomer ("The changing immune system in sepsis: Is individualized immuno-modulatory therapy the answer?", Virulence 5:1, 45-56; Jan. 1, 2014), which is incorporated by reference in its entirety.

In some embodiments, the second immune stimulator is an inhibitor to a checkpoint protein (a.k.a. checkpoint inhibitor, immune checkpoint modulators, or CPMs). As used herein, a checkpoint protein is one that keeps the immune system from attacking the cells. Checkpoint inhibitors are designed to lessen the effectiveness of checkpoint proteins.

In some embodiments, the checkpoint proteins include, but are not limited to, PD1, PDL1, CTLA4, KIR, IDO1, 4-1BB (CD137), OX40 (CD134), and LAG3.

In some embodiments, the second immunostimulants are capable of attenuating abnormal immune suppression in the subject. In some embodiments, the abnormal immune suppression is due to abnormally high activity of an immune suppressor in the immune system. In some embodiments, the immune suppressor with abnormally high activity in the subject is programmed death receptor (PD-1), programmed death ligand (PD-L), B and T lymphocyte attenuator (BTLA), herpesvirus entry mediator (HVEM), or cytokine IL-10. In some embodiments, the second immunestimulator effective in treating sepsis is an inhibitor of the immune suppressor that has abnormally high activity in a sepsis patient during the hypo-inflammatory phase, see Boomer ("The changing immune system in sepsis: Is individualized immuno-modulatory therapy the answer?", Virulence 5:1, 45-56; Jan. 1, 2014), which is herein incorporated by reference in its entirety for all purposes. In some embodiments, the second immune stimulator is an inhibitor of PD-1, PD-L, BTLA, HVEM and/or IL-10. In some embodiments, the inhibitor reduces the activity of PD-1, PD-L, BTLA, HVEM and/or IL-10 at DNA level, mRNA level, and/or protein level. In some embodiments, the inhibitor is an antibody against PD-1, PD-L, BTLA, HVEM or IL-10. In some embodiments, the inhibitor is an antibody against PD-1, such as those described in U.S. Pat. Nos. 8,552,154, 8,741, 295, 8,008,449, 8,460,886 and 7,029,674, or U.S. Patent Application Publication Nos. 20110171220, 20110271358, 20140044738, each of which is herein incorporated by reference in its entirety. In some embodiments, the inhibitor is an antibody against the PD ligand. In some embodiments, the inhibitor inhibits the interaction between PD-1 and its ligand.

In some embodiment, the PD-1 inhibitor is an antibody against PD-1. In some embodiments, the dosage of the PD-1 antibody is about 0.1 to 10 mg/kg, such as about 0.1, 0.2, 0.3, 0.4, 0.5, 0.6, 0.7, 0.8, 0.9, 1.0, 2.0, 3.0, 4.0, 5.0, 6.0, 7.0, 8.0, 9.0, or 10 mg/kg. In some embodiments, the dosage of PD-1 antibody is about 1-5 mg/kg, or about 2-3 mg/kg.

As used herein, the phrase "an inhibitor of PD-1" refers to a compound that inhibits the signaling pathway mediated by PD-1, such as an inhibitor to a component in the PD-1 signaling pathway. The PD-1 signaling pathway is described in Riley (Immunol Rev. 2009 May; 229(1): 114-125.), which is herein incorporated by reference in its entirety. As used herein, the term "activity" of a component in the PD-1 signaling pathway can be a parameter at genomic DNA level, transcriptional level, post-transcriptional level, translational level, post-translational level, including, but not limited to gene activity, RNA activity, and protein activity. The gene activity can be gene copy number, gene amplification number, or promoter activity, etc. RNA activity can be mRNA abundance, synthesis rate, and/or stability, etc. Protein activity can be protein abundance, synthesis rate, stability, enzymatic activity, phosphorylation rate, modifications, binding activity, etc. In some embodiments, the inhibitors reduce the activity of PD-1. In some embodiments, the inhibitors reduce the activity of a ligand for PD-1. In some embodiments, the inhibitor is a PD-1 inhibitor, such as an anti-PD-1 antibody, or an inhibitor of the ligand for PD-1 (a.k.a. PDL-1), such as an anti-PDL-1 antibody. The antibody can be either monoclonal, polyclonal, or a combination thereof.

In some embodiments, the second immune stimulator is a cytokine. In some embodiments, cytokines include, but are not limited to, chemokines, interferons, interleukins, lymphokines, tumour necrosis factor.

In some embodiments, the cytokine as the second immune stimulator is a colony-stimulating factor (CSF). As used herein, the term CSF refers to isolated, synthetic, or recombinant CSFs, including functional derivatives and functional fragments thereof. As used herein, the term CSF refers to substances comprising either a full length colony stimulating factor polypeptide, functional fragment thereof, and/or functional derivatives thereof. Colony stimulating factors are secreted glycoproteins that bind to receptor proteins on the surfaces of hemopoietic stem cells, thereby activating intracellular signaling pathways that lead to cell proliferation and/or differentiation into specific kind of blood cells, such as white blood cells.

In some embodiments, the CSF comprise a polypeptide of macrophage colony-stimulating factors (e.g., CSF1, or M-CSF), granulocyte macrophage colony-stimulating factors (e.g., CSF2, a.k.a. GM-CSF), granulocyte colony-stimulating factors (e.g., CSF3, a.k.a. GCSF, or G-CSF), and/or analogs thereof, such as promegapoietin or filgrastim, or a functional fragment thereof capable of stimulate immune system in a subject.

In some embodiments, the cytokine as the second immune stimulator is GM-CSF. As used herein, the term GM-CSF refers to isolated, synthetic, or recombinant GM-CSFs, including functional derivatives and functional fragments thereof. Naturally, GM-CSF can be secreted by macrophages, T cells, mast cells, NK cells, endothelial cells and fibroblasts. In some embodiments, the immune stimulator can be pharmaceutical analogs of natural GM-CSF, such as sargramostim and molgramostim. In some embodiments, the GM-CSF is in the form of homodimer or heterodimer. In some embodiments, the GM-CSF is manufactured using recombinant technology (e.g., molgramostim or sargramostim (a.k.a., leukine)).

In some embodiment, the dosage of GM-CSF is about 1 to 1000 mcg/m$^2$, such as about 5, 10, 20, 30, 40, 50, 60, 70, 80, 90, 100, 200, 300, 400, 500, 600, 700, 800, 900, 1000 mcg/m$^2$. In some embodiments, the dosage of GM-CSF is about 125 to about 250 mcg/m$^2$.

In some embodiments, the cytokine as the second immune stimulator is an interferon. As used herein, the term interferon refers to isolated, synthetic, or recombinant interferons, including functional derivatives and functional fragments thereof. As used herein, interferons (IFNs) refer to polypeptides made and released by host cells in response to the presence of pathogens, such as viruses, bacteria, parasites or tumor cells. In some embodiments, the interferon activates immune cells. In some embodiments, the interferon activates natural killer cells and macrophages. In some embodiments, the interferon increases the activity of major histocompatibility complex (MHC) antigents. In some embodiments, the interferon belongs to Type I IFN, Type II IFN, or Type III IFN. In some embodiments, the Type I IFN is IFN-α, IFN-β, IFN-ε, IFN-κ, or IFN-ω. In some embodiments, the Type II IFN binds to IFNR that consists of IFNFGR1 and IFNGR2 chains, such as IFN-γ. In some embodiments, the Type III IFN signals through a receptor complex consisting of CRF2-4 and IFNLLR1. In some embodiments, an interferon of the present application increase the activity of MHC I and/or MHC II activity. In some embodiments, the interferon increases the immunoproteasome activity in the subject. In some embodiments, the interferon increases the activity of cytotoxic T cells. In some embodiments, the interferon activates signal transducer and activator of transcription (STAT) complexes. In some embodiments, the interferon activates Janus kinase-STAT (JAK-STAT) signaling pathway. In some embodiments, the interferon activates the CRK family of adaptor protein CRKL, which is a nuclear adaptor for STATS that also regulates signaling through the C3G/Rap1 pathway. In some embodiments, the interferon activates the p38 mitogen-activated protein kinase (MAP kinase) to induce gene transcription. In some embodiments, the interferon activates the phosphatidylinositol 3-kinase (PI3K) signaling pathway. In some embodiments, the interferon increases the activity of helper T cells. In some embodiments, the interferon is IFN-γ. In some embodiments, the interferons directly activate macrophages and/or natural killer cells. In some embodiments, the immune stimulator can induce interferons. In some embodiments, the interferon is linked to polyethylene glycol.

In some embodiments, the cytokine as the second immune stimulator is a tumor necrosis factor (TNF). As used herein, the term TNF refers to isolated, synthetic, or recombinant TNF, including functional derivatives and functional fragments thereof. In some embodiments, the TNF can be produced by activated macrophages, CD4+ lymphocytes, NK cells, neutrophils, mast cells, eosinophils, or neurons.

In some embodiments, the cytokine as the second immune stimulator is an interleukin. As used herein, the term interleukin refers to isolated, synthetic, or recombinant interleukins, including functional derivatives and functional fragments thereof. In some embodiments, the interleukin can be synthesized by helper CD4 T lymphocytes, monocytes, macrophages, or endothelial cells. In some embodiments, the interleukin promotes the development and/or differentiation of T lymphocytes, B lymphocytes, and/or hematopoietic cells. In some embodiments, the immune stimulator comprises interleukin 1, interleukin 3, interleukin 4, interleukin 5, interleukin 6, interleukin 7, interleukin 8, interleukin 9, interleukin 10, interleukin 11, interleukin 12, interleukin 13, interleukin 14, interleukin 15, interleukin 16, or interleukin 17. As used herein, the term interleukin refers to both interleukin isolated, synthetic, or recombinant interleukins, including functional derivatives and functional fragments thereof. In some embodiments, the immune stimulator comprises IL-7, IL-9 and/or IL-15. In some embodiments, the immune stimulator comprises an interleukin that can serve as a growth factor for lymphoid cells, such as B-cell lineages, T-cell lineages and/or NK cells. In some embodiments, the immune stimulator comprises an interleukin that can support growth of helper T cells. In some embodiments, the immune stimulator comprises an interleukin that can stimulate and maintain cellular immune responses. In some embodiments, the immune stimulator comprises an interleukin that can stimulate the proliferation of lymphoid cells, such as B-cell lineages and/or T-cell lineages.

In some embodiments, the second immune stimulator comprises a substance that can enhance the activity of an IL receptor. In some embodiments, the IL receptor is the IL-7 receptor. In some embodiments, the immune stimulator comprises a substance that can enhance the interaction of IL-7 and IL-7 receptor. In some embodiments, the immune stimulator comprises Interleukin-7 receptor alpha. In some embodiments, the immune stimulator comprises common gamma chain receptor, which forms heterodimer with Interleukin-7 receptor alpha. In some embodiments, the IL receptor is the IL-9 receptor. In some embodiments, the immune stimulator comprises a substance that can enhance interaction of IL-9 and IL-9 receptor. In some embodiments, the immune stimulator comprises Interleukin-9 receptor. In some embodiments, the IL receptor is the IL-15 receptor. In some embodiments, the immune stimulator comprises a substance that can enhance the interaction of IL-15 and IL-15 receptor. In some embodiments, the immune stimulator comprises Interleukin-15 receptor beta chain (CD122). In some embodiments, the immune stimulator comprises Interleukin-15 receptor common gamma chain (gamma-C, CD132).

In some embodiments, the second immune stimulator comprises an interleukin. In some embodiments, the interleukin is IL-7. In some embodiment, the dosage of IL-7 is about 0.1 to 100 mcg/kg, such as about 0.1, 0.2, 0.3, 0.4, 0.5, 0.6, 0.7, 0.8, 0.9, 1, 2, 3, 4, 5, 6, 7, 8, 9, 10, 20, 30, 40, 50, 60, 70, 80, 90, or 100 mcg/kg. In some embodiment, the dosage is about 1 to 50 mcg/kg, or about 3 to 30 mcg/kg.

Other immune stimulators can be used. In some embodiments, the immune stimulator can function as a white blood cell growth factor. In some embodiments, the immune stimulator stimulates stem cells to produce granulocytes (e.g., neutrophils, eosinophils, and basophils) and/or monocytes. In some embodiments, the immune stimulator can prevent neutropenia following chemotherapy. In some embodiments, the immune stimulator can stimulates the survival, proliferation, differentiation, and/or function of neutrophil precursors and mature neutrophils. In some embodiments, the immune stimulator functions by using one or more signaling pathways including but not limited to, Janus kinase (JAK), signal transducer and activator of transcription (STAT), Ras/mitogen-activated protein kinase (MAPK), phosphatidylinositol 3-kinase (PI3K), and protein kinase B (Akt) signal transduction pathway.

In some embodiments, an immunostimulant or a combination of at least two immunostimulants of the present application is combined with an anti-cancer agent.

In some embodiments, an anti-cancer agent that may be used in combination with a immunostimulant of the present application may include, but are not limited to, estrogen receptor antagonist, receptor tyrosine kinase inhibitors, cancer cell replication inhibitors, cancer cell signaling inhibitors or silences and other inhibitors of tumor cell surface of internal cell signaling molecules implicated in cancer cell growth, cancer cell resistance to apoptosis and/or cancer cell metastases.

In some embodiments, a immunostimulant of the present application is used in combination with an estrogen receptor antagonist (ERANT), an inhibitor to the estrogen receptor, or an inhibitor to the estrogen receptor ligand.

In some embodiments, a immunostimulant of the present application is used in combination with a receptor tyrosine kinase inhibitor. Tyrosine kinase inhibitors represent a class of therapeutic agents or drugs that target receptor and/or non-receptor tyrosine kinases in cells such as tumor cells. In certain instances, the tyrosine kinase inhibitor is an antibody-based (e.g., anti-tyrosine kinase monoclonal antibody, etc.) or polynucleotide-based (e.g., tyrosine kinase antisense oligonucleotide, small interfering ribonucleic acid, etc.) form of targeted therapy. In some embodiments, the tyrosine kinase inhibitor is a small molecule that inhibits target tyrosine kinases by binding to the ATP-binding site of the enzyme.

In some embodiments, a immunostimulant of the present application is used in combination with a cancer cell replication inhibitor, such as anti-microtubule agents, which refer to chemicals that block cell division by preventing microtubule function.

In some embodiments, a immunostimulant of the present application is used in combination with a cancer cell signaling inhibitor. In some embodiments, the cancer cell signaling inhibitor include agents that can inhibit EGFR (epidermal growth factor receptor) responses, such as EGFR antibodies, EGF antibodies, and molecules that are EGFR inhibitors; VEGF (vascular endothelial growth factor) inhibitors; and erbB2 receptor inhibitors, such as organic molecules or antibodies that bind to the erbB2 receptor.

In some embodiments, the additional anti-cancer agent can be administered prior to, concurrently, or after the administration of a first immune stimulator of the present invention.

In some embodiments, the anti-cancer agent comprises ipilimymab or derivatives as described in U.S. Pat. Nos. 7,611,702, 7,741,345, and 8,088,770, which are incorporated by reference in their entireties.

In some embodiments, the anti-cancer agent comprises a signal transduction inhibitor. In some embodiments, the transduction inhibitor is a BRAF inhibitor, such as vemurafenib and dabrafenib. In some embodiments, the transduction inhibitor is a MEK inhibitor, such as trametinib. In some embodiments, the transduction inhibitor is a c-KIT inhibitor, such as imatinib.

In some embodiments, the anti-cancer agent comprises a kinase inhibitor. In some embodiments, the kinase inhibitor comprises sorafenib or derivatives as described in U.S. Pat. No. 7,235,576. The kinase inhibitor may be administered continuously (i.e., daily), multiple times per day, every other day, etc., and may be administered prior to, concurrently, or after administration of an immune stimulator of the present, e.g., on the same day(s) or on different days during the course of the treatment regimen. In certain embodiments, the kinase inhibitor is administered in a dosage range of, e.g., about 10-2000 mg/day of administration, about 50-1000 mg/day, or about 50-800 mg/day. Daily dosages may be, e.g., about 50 mg, 100 mg, 200 mg, 300 mg, 400 mg, 500 mg, 600 mg, 700 mg, 800 mg, etc.

In some embodiments, the anti-cancer agent comprises an antineoplastic heat shock apoptosis activator (HSAA), see US Patent Application Publication No. 20100317583, which is herein incorporated by reference in its entirety. In some embodiments, the HSAA comprises STA-4783 (elesclomol). The HSAA may be administered continuously (i.e., daily), multiple times per day, every other day, etc., and may be administered prior to, concurrently, or after administration of an immune stimulator of the present, e.g., on the same day(s) or on different days during the course of the treatment regimen. In certain embodiments, the HSAA is administered in dosage ranges of, e.g., about 0.01-1000 mg/kg/day of administration, about 0.1-500 mg/kg/day, or about 1-200 mg/kg/day. Daily dosages may be, e.g., 25 mg/kg, 100 mg/kg, etc.

In some embodiments, the anti-cancer agent comprises an inhibitor against cytotoxic T lymphocyte-associated antigen 4 (CTLA4), see US Patent Application Publication No. 20100330093, which is herein incorporated by reference in its entirety. In some embodiments, the inhibitor is an antibody against CTLA4. In some embodiments, the CTLA4 antibodies include, but are not limited to, 9H10 (EBIOSCIENCE), MDX010 (MEDAREX), 1F4 (GENETEX), BNI3 (GENETEX), Q01 (ABNOVA), A01 (ABNOVA), M08 (ABNOVA), 1B8 (ABCAM), WKH203 (ABCAM), ab9984 (ABCAM), ab13486 (ABCAM), ipilimumab, ticilimumab or a combination thereof. In some embodiments, the CTLA4 antibodies may be administered continuously (i.e., daily), multiple times per day, every other day, etc., and may be administered prior to, concurrently, or after administration of an immune stimulator of the present, e.g., on the same day(s) or on different days during the course of the treatment regimen. In some embodiments, the CTLA4 antibodies are administered in a dosage range of, e.g., 0.001-50 mg/kg patient body weight per day of administration, or about 0.01-20 mg/k, or about 1-15 mg/kg.

In certain embodiments, the anti-cancer agent comprises one or more antineoplastic agents. In some embodiments, the antineoplastic agents are chemotherapeutics. In some embodiments, the chemotherapeutics are selected from alkylating agents, anti-metabolites, anti-microtubule agents, Topoisomerase inhibitors, and Cytotoxic antibiotics.

As used herein, the term "alkylating agents" refers to agents that have the ability to alhylate molecules in a subject, including proteins, RNA and DNA. Non-limiting examples of alkylating agents include nitrogen mustards, nitrosoureas, tetrazines, aziridines, cisplatins and derivatives, and non-classical alkylating agents. Nitrogen mustards include mechlorethamine, cyclophosphamide, melphalan, chlorambucil, ifosfamide and busulfan.

As used herein, the term "anti-metabolites" refers to molecule that impedes DNA, RNA, or protein synthesis. In some embodiments, anti-metabolites resemble either nucleobases or nucleosides (a nucleotide without the phosphate group), but have altered chemical groups. These drugs exert their effect by either blocking the enzymes required for DNA synthesis or becoming incorporated into DNA or RNA. By inhibiting the enzymes involved in DNA synthesis, they prevent mitosis because the DNA cannot duplicate itself. Also, after misincorporation of the molecules into DNA, DNA damage can occur and programmed cell death (apoptosis) is induced. In some embodiments, the anti-metabolites are anti-folates, fluoropyrimidines, deoxynucleoside analogues and thiopurines. In some embodiments, the anti-metabolites are selected from methotrexate, pemetrexed, fluorouracil, capecitabine, cytarabine, gemcitabine, decitabine, Vidaza, fludarabine, nelarabine, cladribine, clofarabine, pentostatin, thioguanine and mercaptopurine.

As used herein, the term "anti-microtubule agents" refers to chemicals that block cell division by preventing microtubule function.

In some embodiments, the anti-tumor agents are mitotic inhibitors.

As used herein, the term "topoisomerase inhibitors" refers to agents that can modulate the activity of topoisomerase I and/or topoisomerase II. In some embodiments, the topoisomerase inhibitor of this invention can be a topoisomerase I inhibitor. In further embodiments of this invention, the topoisomerase inhibitor is a topoisomerase II inhibitor.

As used herein, the term "cytotoxic antibiotics" cytotoxic antibiotics include, but are not limited to, antinomycin, bleomycin, mitomycin, plicamycin and the like. Examples of tyrosine kinase inhibitors include, but are not limited to, nilotinib, imatinib, gefitinib, erlotinib, cetuximab, panitumumab, zalutumumab, nimotuzumab, matuzuman and the like.

In some embodiments, the other anti-cancer agents are monoclonal antibodies, such as alemtuzumab, bevacizumab, cetuximab, gemtuzumab, rituximab, and trastuzumab; photosensitizers, such as aminolevulinic acid, methyl aminolevulinate, porfimer sodium, and verteporfin; and other agents, such as alitretinoin, altretamine, amsacrine, anagrelide, arsenic trioxide, asparaginase, bexarotene, bortezomib, celecoxib, denileukin diftitox, erlotinib, estramustine, gefitinib, hydroxycarbamide, imatinib, pentostatin, masoprocol, mitotane, pegaspargase, and tretinoin.

In some embodiments, the antineoplastic agent comprises alkylating antineoplastic agents (AlkAA). In some embodiments, the AlkAA comprises dacarbazine (DTIC). In some embodiments, an alkylating antineoplastic agent may be administered to patient within a dosage range of, e.g., about 700-1300 mg/m2/day, more preferably in a dosage range of about 800-1200 mg/m2/day, and most preferably about 1000 mg/m2/day.

In some embodiments, a pharmaceutical composition of the present invention can ameliorate, treat, and/or prevent one or more symptoms of melanoma in a clinically relevant, statistically significant and/or persistent fashion. In some embodiments, administration of a pharmaceutical composition of the present invention provides statistically significant therapeutic effect for ameliorating, treating, and/or preventing one or more symptoms of melanoma. In one embodiment, the statistically significant therapeutic effect is determined based on one or more standards or criteria provided by one or more regulatory agencies in the United States, e.g., FDA or other countries. In some embodiments, the statistically significant therapeutic effect is determined based on results obtained from regulatory agency approved clinical trial set up and/or procedure. In some embodiments, a pharmaceutical composition of the present invention provides statistically significant therapeutic effect as measured by recurrence-free survival (RFS, the length of time before recurrence or death). In some embodiments, a pharmaceutical composition of the present invention provides statistically significant therapeutic effect as measured by frequency and/or severity of metastases.

In some embodiments, the statistically significant therapeutic effect is determined based on a patient population of at least 50, 100, 200, 300, 400, 500, 600, 700, 800, 900, 1000, or more. In some embodiments, the statistically significant therapeutic effect is determined based on data obtained from randomized and double blinded clinical trial set up. In some embodiments, the statistically significant therapeutic effect is determined based on data with a p value of less than or equal to about 0.05, 0.04, 0.03, 0.02 or 0.01. In some embodiments, the statistically significant therapeutic effect is determined based on data with a confidence interval greater than or equal to 95%, 96%, 97%, 98% or 99%. In some embodiments, the statistically significant therapeutic effect is determined on approval of Phase III clinical trial of the methods provided by the present invention, e.g., by FDA in the US.

In some embodiment, the statistically significant therapeutic effect is determined by a randomized double blind clinical trial of a patient population of at least 50, 100, 200, 300 or 350; treated with a pharmaceutical composition of the present invention, but not in combination with any other agent for treating MD symptoms. In some embodiment, the statistically significant therapeutic effect is determined by a randomized clinical trial of a patient population of at least 50, 100, 200, 300 or 350 and using any commonly accepted criteria for MD symptoms assessment, such as the criteria described herein.

In general, statistical analysis can include any suitable method permitted by a regulatory agency, e.g., FDA in the US or China or any other country. In some embodiments, statistical analysis includes non-stratified analysis, log-rank analysis, e.g., from Kaplan-Meier, Jacobson-Truax, Gulliken-Lord-Novick, Edwards-Nunnally, Hageman-Arrindel and Hierarchical Linear Modeling (HLM) and Cox regression analysis.

In some embodiments, the methods comprise administering the immune stimulator at a specific phase of the melanoma progression. In some embodiments, the immune stimulator is administered to the subject when apoptosis of T-cells in the subject starts. Methods of detecting apoptosis of T-cells are well known, such as those using FITC Annexin V. In some embodiments, the immune stimulator is administered to the subject when the subject experiences T-cell exhaustion due to apoptosis of T-cells. Methods of T-cells quantification are well known, such as those using flow cytometry. In some embodiments, the immune stimulator is administered to the subject in order to maintain a predetermined level of active T-cell populations in the subject. In some embodiments, the activated T-cells are CD8+ T-cells and/or CD4+ T-cells.

In certain embodiments, the treatment regimen comprises a plurality of days of a pharmaceutical composition comprising an immune stimulator of the present invention, and the immune stimulator can be administered to the subject during at least a portion of the treatment regimen.

In certain embodiments, the treatment regimen comprises administering the pharmaceutical composition for a period of about 1-10 days, about 1-20 days, about 1-30 days, about 1-40 days, about 1-50 days, about 1-60 days, about 1-70 days, about 1-80 days, about 1-90 days, about 1-100 days, or more.

In certain embodiments, the treatment regimen further comprises about 1-5 days, about 5-10 days, about 10-20 days, about 20-30 days or more of non-administration of the pharmaceutical composition. In some embodiments, the pharmaceutical composition may be administered daily for 1-10 days, about 1-20 days, about 1-30 days, about 1-40 days, about 1-50 days, about 1-60 days, about 1-70 days, about 1-80 days, about 1-90 days, about 1-100 days, or more, followed by about 1-5 days, about 5-10 days, about 10-20 days, about 20-30 days of non-administration of the alpha thymosin peptide.

In some embodiments, the methods further comprise monitoring the response of the subject after administration to avoid severe and/or fatal immune-mediated adverse reactions due to over-activation and proliferation. In some embodiments, the administration of the immune stimulator is modified, such as reduced, paused or terminated if the patient shows persistent moderate adverse reactions. In some embodiments, the dosage is modified if the patient fails to respond within about 1 week, 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks or more from administration of first dose. In some embodiments, the dosage is modified if the patient shows severe or life-threatening adverse reactions, including but not limited to, colitis with abdominal pain, fever, ileus, or peritoneal signs; increase in stool frequency (≥7 over baseline), stool incontinence, need for intravenous hydration for >24 hours, gastrointestinal hemorrhage, and gastrointestinal perforation, AST or ALT>5× the upper limit of normal (ULN) or total bilirubin>3× the ULN, Stevens-Johnson syndrome, toxic epidermal necrolysis, or rash complicated by full-thickness dermal ulceration or necrotic, bullous, or hemorrhagic manifestations, severe motor or sensory neuropathy, Guillain-Barré syndrome, myasthenia gravis, severe immune-mediated reactions involving any organ system immune-mediated ocular disease which is unresponsive to topical immunosuppressive therapy.

In some embodiments, the methods comprise determining the activity of one or more components in the immune system before, during, and/or after administration of an immune stimulator of the present invention. In some embodiments, a treatment regimen of the present invention can be modified based on the activity of one or more components in the immune system. In some embodiments, the components in the immune system includes, but are not limited to T-cell apoptosis, CD+8 T-cells, and CD+4 T-cells. In some embodiments, the methods comprise determining one or more biomarkers indicating the activity of T-cell apoptosis, CD+8 T-cells, and/or CD+4 T-cells. In some embodiments, the methods comprise determining the activity of effector T cells. In some embodiments, the methods comprise determining the activity of helper T cells.

In some embodiments, the activity of one or more components in the immune system subject is compared to a pre-determined standard to decide if a pharmaceutical composition of the present invention should be administered to the subject and/or when the pharmaceutical composition can be administered to the subject. In some embodiments, the component can be IL-2, IL-2 receptor, IL-7, IL-7 receptor, IL-15, IL-15 receptor, CD69, IFNγ, IL-6, TNF, IL-1, GM-CSF, PD-L, PD-1, IL-10, BTLA, HVEM, IL-1β, IL-4, IL-6, IL-10, or combinations thereof. In some embodiments, a pharmaceutical composition of the present invention is administered to a subject when the activity of PD-L, PD-1, IL-10 TLA, and/or HVEM is higher compared to the pre-determined standard. In some embodiments, a pharmaceutical composition of the present invention is administered to a subject when the activity of IL-2, IL-2 receptor, IL-7, IL-7 receptor, IL-15, IL-15 receptor, CD69, IFNγ, IL-6, TNF, and/or GM-CSF is lower compared to the pre-determined standard. In some embodiments, a pharmaceutical composition of the present invention is administered to a subject when the activity of IL-1β is higher compared to the pre-determined standard. In some embodiments, a pharmaceutical composition of the present invention is administered to a subject when the activity of IL-4 is lower compared to the pre-determined standard. In some embodiments, a pharmaceutical composition of the present invention is administered to a subject when the activity of IL-6 is higher compared to the pre-determined standard. In some embodiments, a pharmaceutical composition of the present invention is administered to a subject when the activity of IL-10 is higher compared to the pre-determined standard.

In some embodiments, treatment methods of the present invention are combined with one or more additional treatments for cancer. In some embodiments, the additional treatment is surgery. In some embodiments, the additional treatment is an adjuvant treatment. In some embodiments, the additional treatment is chemotherapy. In some embodiments, the additional treatment is immunotherapy. In some embodiments, the additional treatment is radiation therapy. In some embodiments, the additional treatment is a targeted therapy, such as adoptive cell therapy or gene therapy.

In certain embodiments, the subject is immunodeficient. An immunodeficient subject (e.g., a human subject) exhibits a reduced capacity to fight infectious disease and/or a reduced capacity to respond to pathogen exposure. Examples of such immunodeficient subjects include an elderly patient, newborn, leukemic or neutropenic patient, a patient on hemodialysis (e.g., for treatment of chronic renal disease), patient receiving immunosuppressant therapy, AIDS patient, diabetic patient, patient receiving chemotherapy or radiation therapy for cancer, immunodeficiency caused by a genetic defect, malnutrition, drug abuse, alcoholism, or other immune-compromising illness or condition.

In certain embodiments, the immune-compromised subject is elderly. As animals age, their immune response is reduced, and the robustness of the immune response is diminished due to the prevalence of low affinity antibody response. Accordingly, the subject in these embodiments may be a human patient over the age of 45, or over the age of 50. In some embodiments, the subject is a human patient 60 years of age or older, 65 years of age or older, or 70 years of age or older.

In certain embodiments, the treatment regimen further comprises determine the patient response during the treatment. In some embodiments, one or more symptoms associated with the infection are evaluated to determine the subject's response to the treatment regimen.

In some embodiments, a composition of the present invention induces a strong and rapid immune response to pathogens in the subject or the population of subjects. The regimen of thymosin as described herein provides the patient with a more robust immune response to pathogen exposure, including but not limited to, higher antibody titers and/or a more rapid antibody response. In some embodiments, the regimen provides such advantages for up to about 10 days, 20 days, 30 days, 40 days, 50 days or more with as few as one, two, three, or four administrations.

In some embodiments, the subject has been diagnosed as having a cancer. In some embodiments, the cancer is melanoma.

In some embodiments, a composition of the present invention is administered by any suitable methods known in the art. In some embodiments, administration of a composition of the present invention may be carried out orally, parenterally, subcutaneously, intravenously, intramuscularly, intraperitoneally, by intranasal instillation, by implantation, by intracavitary or intravesical instillation, intraocularly, intraarterially, intralesionally, transdermally, or by application to mucous membranes. The inhibitor may be administered with a pharmaceutically-acceptable carrier. In some embodiments, the thymosin is administered to a subject by injection (e.g., intramuscular, intraarterial, intravascular, intravenous, intraperitoneal, or subcutaneous). By "pharmaceutically acceptable" is meant a material that is not biologically or otherwise undesirable, i.e., the material may be incorporated into a pharmaceutical composition administered to a patient without causing any significant undesirable biological effects or interacting in a deleterious manner with any of the other components of the composition in which it is contained. When the term "pharmaceutically acceptable" is used to refer to a pharmaceutical carrier or excipient, it is implied that the carrier or excipient has met the required standards of toxicological and manufacturing testing or that it is included on the Inactive Ingredient Guide prepared by the U.S. Food and Drug administration.

In some embodiments, a composition of the present invention can be provided in pharmaceutical compositions comprising a vehicle, such as an artificial membrane vesicle (including a liposome, lipid micelle and the like), microparticle or microcapsule.

Compositions intended for oral use may be prepared in either solid or fluid unit dosage forms. Fluid unit dosage form can be prepared according to procedures known in the art for the manufacture of pharmaceutical compositions and such compositions may contain one or more agents selected from the group consisting of sweetening agents, flavoring agents, coloring agents and preserving agents in order to provide pharmaceutically elegant and palatable preparations. An elixir is prepared by using a hydroalcoholic (e.g., ethanol) vehicle with suitable sweeteners such as sugar and saccharin, together with an aromatic flavoring agent. Suspensions can be prepared with an aqueous vehicle with the aid of a suspending agent such as acacia, tragacanth, methylcellulose and the like.

Solid formulations such as tablets contain the active ingredient in admixture with non-toxic pharmaceutically acceptable excipients that are suitable for the manufacture of tablets. These excipients may be for example, inert diluents, such as calcium carbonate, sodium carbonate, lactose, calcium phosphate or sodium phosphate: granulating and disintegrating agents for example, corn starch, or alginic acid: binding agents, for example starch, gelatin or acacia, and lubricating agents, for example magnesium stearate, stearic acid or talc and other conventional ingredients such as dicalcium phosphate, magnesium aluminum silicate, calcium sulfate, starch, lactose, methylcellulose, and functionally similar materials. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil. Soft gelatin capsules are prepared by machine encapsulation of a slurry of the compound with an acceptable vegetable oil, light liquid petrolatum or other inert oil.

Aqueous suspensions contain active materials in admixture with excipients suitable for the manufacture of aqueous suspensions. Such excipients are suspending agents, for example sodium carboxylmethylcellulose, methyl cellulose, hydropropylmethylcellulose, sodium alginate, polyvinylpyrrolidone, gum tragacanth and gum acacia: dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example hepta-decaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl-p-hydroxy benzoate, one or more colouring agents, one or more flavoring agents or one or more sweetening agents, such as sucrose or saccharin.

Oily suspensions may be formulated by suspending the active ingredients in a vegetable oil, for example peanut oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and colouring agents, may also be present.

Pharmaceutical compositions of the invention may also be in the form of oil-in-water emulsions. The oil phase may be a vegetable oil, for example olive oil or peanut oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions may also contain sweetening and flavoring agents.

The pharmaceutical compositions may be in the form of a sterile injectable aqueous or oleaginous suspension. This suspension may be formulated according to known art using those suitable dispersing or wetting agents and suspending agents that have been mentioned above. The sterile injectable preparation may also be a sterile injectable solution or a suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables. Adjuvants such as local anaesthetics, preservatives and buffering agents can also be included in the injectable solution or suspension.

In some embodiments, the delivery systems suitable include time-release, delayed release, sustained release, or controlled release delivery systems. In some embodiments, a composition of the present invention can be delivered in a controlled release system, such as sustained-release matrices. Non-limiting examples of sustained-release matrices include polyesters, hydrogels (e.g., poly(2-hydroxyethyl-methacrylate) as described by Langer et al., 1981, J. Biomed. Mater. Res., 15:167-277 and Langer, 1982, Chem. Tech., 12:98-105), or poly(vinylalcohol)], polylactides (U.S. Pat. No. 3,773,919; EP 58,481), copolymers of L-glutamic acid and gamma ethyl-L-glutamate (Sidman et al., 1983, Biopolymers, 22:547-556), non-degradable ethylene-vinyl acetate (Langer et al., supra), degradable lactic acid-glycolic acid copolymers such as the LUPRON DEPOT™ (injectable microspheres composed of lactic acid-glycolic acid copolymer and leuprolide acetate), and poly-D-(-)-3-hydroxybutyric acid (EP 133,988). In some embodiments, the composition may be administered using intravenous infusion, an implantable osmotic pump, a transdermal patch, liposomes, or other modes of administration. In one embodiment, a pump may be used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989). In another embodiment, polymeric materials can be used. In yet another embodiment, a controlled release system can be placed in proximity to the therapeutic target, for example liver, thus requiring only a fraction of the systemic dose (see, e.g., Goodson, in Medical Applications of Controlled Release, supra, vol. 2, pp. 115-138 (1984). Other controlled release systems are discussed in the review by Langer (Science 249:1527-1533 (1990). In some embodiments, the composition may be administered through subcutaneous injection.

In some embodiments, the release of the composition occurs in bursts. Examples of systems in which release occurs in bursts includes, e.g., systems in which the composition is entrapped in liposomes which are encapsulated in a polymer matrix, the liposomes being sensitive to specific stimuli, e.g., temperature, pH, light or a degrading enzyme and systems in which the composition is encapsulated by an ionically-coated microcapsule with a microcapsule core degrading enzyme.

In some embodiments, the release of the composition is gradual/continuous. Examples of systems in which release of the inhibitor is gradual and continuous include, e.g., erosional systems in which the composition is contained in a form within a matrix and effusional systems in which the composition is released at a controlled rate, e.g., through a polymer. Such sustained release systems can be e.g., in the form of pellets, or capsules.

Other embodiments of the compositions administered according to the invention incorporate particulate forms, protective coatings, protease inhibitors or permeation enhancers for various routes of administration, such as parenteral, pulmonary, nasal and oral. Other pharmaceutical compositions and methods of preparing pharmaceutical compositions are known in the art and are described, for example, in "*Remington: The Science and Practice of Pharmacy*" (formerly "*Remingtons Pharmaceutical Sciences*"); Gennaro, A., Lippincott, Williams & Wilkins, Philidelphia, Pa. (2000). In some embodiments, the pharmaceutical composition may further include a pharmaceutically acceptable diluent, excipient, carrier, or adjuvant.

The dosage to be administered is not subject to defined limits, but it will usually be an effective amount, or a therapeutically/pharmaceutically effective amount. The term "effective amount" refers to the amount of one or more compounds that renders a desired treatment outcome. An effective amount may be comprised within one or more doses, i.e., a single dose or multiple doses may be required to achieve the desired treatment endpoint. The term "therapeutically/pharmaceutically effective amount" as used herein, refers to the level or amount of one or more agents needed to treat a condition, or reduce or prevent injury or damage, optionally without causing significant negative or adverse side effects. It will usually be the equivalent, on a molar basis of the pharmacologically active free form produced from a dosage formulation upon the metabolic release of the active free drug to achieve its desired pharmacological and physiological effects. In some embodiments, the compositions may be formulated in a unit dosage form. The term "unit dosage form" refers to physically discrete units suitable as unitary dosages for human subjects and other mammals, each unit containing a predetermined quantity of active material calculated to produce the desired therapeutic effect, in association with a suitable pharmaceutical excipient.

In some embodiments, dosing regimen of thymosin includes, without any limitation, the amount per dose, frequency of dosing, e.g., per day, week, or month, total amount per dosing cycle, dosing interval, dosing variation, pattern or modification per dosing cycle, maximum accumulated dosing, or warm up dosing, or any combination thereof. In some other embodiments, dosing regimen of thymosin includes frequency of dosing, e.g., per day or per week.

In yet some embodiments, dosing regimen includes a pre-determined or fixed amount per dose in combination with a frequency of such dose. For example, dosing regimen of thymosin includes a fixed amount per dose in combination with the frequency of such dose of thymosin being administered to a subject.

In some embodiments, effective amounts of thymosin are amounts which may be dosage units within a range corresponding to about 0.1-20 mg of TA1, about 1-10 mg of TA1, about 2-10 mg of TA1, about 2-7 mg of TA1, or about 3-6.5 mg of TA1, and may comprise about 1.6, 3.2 or 6.4 mg of TA1, or about 3.2 or 6.4 mg of TA1. A dosage unit may be administered once per day, or a plurality of times per day. In some embodiments, TA1 is administered to a subject at a dosage within a range of about 0.5-10 mg/day. In certain embodiments, the TA1 dosage is within a range of about 1.5-7 mg/day, or within a range of about 1.6-6.4 mg/day. In certain embodiments, the TA1 dosage is within a range of about 1.7-10 mg/day, about 1.7-7 mg/day, or about 3-7 mg/day. In some embodiments, the effective dosages include about 1.6, 3.2 or 6.4 mg/day.

In some embodiments, the administration provides a serum level of thymosin at about 0.1 to 1.0 ng/ml. In some embodiments, the administration provides a peak plasma level after injection of about 100 ng/ml. In some embodiments, the half-life of TA1 in the circulation is about 2 hours.

In certain embodiments, the treatment regimen comprises a plurality of days of a pharmaceutical composition comprising TA1, or TA1 can be administered to the subject during at least a portion of the treatment regimen.

In certain embodiments, the treatment regimen comprises administering the pharmaceutical composition for a period of about 1-10 days, about 1-20 days, about 1-30 days, or more.

In certain embodiments, the treatment regimen further comprises about 1-5 days, about 5-10 days, about 10-20 days, about 20-30 days or more of non-administration of the pharmaceutical composition. In some embodiments, the pharmaceutical composition may be administered daily, once per two days, once per three days, once per four days, once per five days, once per six days, once per week, for about 1-10 days, about 1-20 days, or more, followed by about 1-5 days, about 5-10 days of non-administration of the thymosin.

In some embodiments, the methods further comprise monitoring the response of the subject after administration to avoid severe and/or fatal immune-mediated adverse reactions due to over-activation and proliferation. In some embodiments, the administration of the immune stimulator is modified, such as reduced, paused or terminated if the patient shows persistent moderate adverse reactions. In some embodiments, the dosage is modified if the patient fails to respond within about 1 day, 2 days, 3 days, 4 days, 5 days, 6 days, 1 week, 2 weeks or more from administration of first dose.

The pharmaceutical composition of the present invention may also alleviate, reduce the severity of, or reduce the occurrence of, one or more of the symptoms associated with melanoma. In some embodiments, such symptoms include, but are not limited to, early signs of melanoma are changes to the shape or color of existing moles or, in the case of nodular melanoma, the appearance of a new lump anywhere on the skin (such lesions should be referred without delay to a dermatologist). At later stages, the mole may itch, ulcerate or bleed. Early signs of melanoma include, but not limited to asymmetry in shape, irregular borders, variegated color, greater than 6 mm diameter, and evolving over time.

In some embodiments, methods of the present invention prevent metastasis, or reduce the rate and/or severity of metastasis.

The present invention also provides a collection of activity profiles of a panel of biomarkers. As used herein, the term "activity profile" refers to a set of data representing distinctive features or characteristics of one or more biomarkers. Such features or characteristics include, but are not limited to, transcript abundance, transcript stability, transcription rate, translation rate, post-translation modification, protein abundance, protein stability, and/or protein enzymatic activity, etc. In some embodiments, the activity profile comprises data related to gene expression level of each biomarker. In some embodiments, the collection comprising activity profiles is obtained from a specific population of subjects. In some embodiments, the specific population of subjects consists of clinically normal subjects. In some embodiments, the population consists of patents responsive to one or more anti-melanoma agents of the present invention. In some embodiments, the population consists of patients not responsive to one or more anti-melanoma agents of the present invention.

In some embodiments, the collection comprises activity profiles that are statistically homogeneous in one or more aspects, e.g., statistically homogeneous in one or more quantitative or semi-quantitative parameters describing the features and characteristics of the activity profiles. In some embodiments, the quantitative parameters include, but are not limited to, transcript abundance, transcript stability, transcription rate, translation rate, post-translation modification, protein abundance, protein stability, and/or protein enzymatic activity, etc. Whether a group of activity profiles are statistically homogeneous or not in one or more aspects can be determined by any suitable statistic test and/or algorithm known to one skilled in the art.

In some embodiments, one or more of the biomarkers increase its activity in response to the treatment. In some embodiments, one or more of the biomarkers decrease its activity in response to the treatment. In some embodiments, one or more of the biomarkers remains its activity in response to the treatment. As used herein, the activity of a biomarker can be a parameter at genomic DNA level, transcriptional level, post-transcriptional level, translational level, post-translational level, including, but not limited to gene activity, RNA activity, and protein activity. The gene activity can be gene copy number, gene amplification number, or promoter activity, etc. RNA activity can be mRNA abundance, synthesis rate, and/or stability, etc. Protein activity can be protein abundance, synthesis rate, stability, enzymatic activity, phosphorylation rate, modifications, binding activity, etc.

As used herein, when the level of a biomarker goes toward the level of a predetermined standard level, it is called normalization.

As used herein, when the level of a biomarker reduces its speed of going away from the level of a predetermined standard level, it is called stabilization.

In some embodiments, the activity profiles of one or more biomarkers of the present invention in a subject are determined and compared to a predetermined standard level. As used herein, the term "predetermined standard level" or "predetermined activity profiles" refers to standardized data or data set representing the average, representative features or characteristics of one or more biomarkers in a specific population. Such features or characteristics include, but are not limited to, gene copy number, gene amplification, transcript abundance, transcript stability, transcription rate, translation rate, post-translation modification, protein abundance, protein stability, and/or protein enzymatic activity, etc. In some embodiments, the specific population of subjects are consisting of about 5, about 10, about 20, about 50, about 100, about 200, about 300, about 400, about 500, about 1000, about 5000, about 10K, or more individual subjects. The predetermined activity profile can be a standardized data or data set collected before, during, or after the specific population of subjects has been all exposed to a drug. In some embodiments, the specific population is consisting of subjects responsive to a given drug.

In some embodiments, a subject is "responsive" to a drug for treating when the level of one or more of the biomarkers of the present invention increases or decreases toward a pre-determined standard level when the subject is exposed to a the drug, or when the drug modifies the speed of level changes of one or more biomarkers of the present invention compared to a placebo. For methods related to detection, quantitation and comparison of biomarker levels, see, e.g., *Current Protocols in Molecular Biology*, Ed. Ausubel, Frederick M. (2010); *Current Protocols in Protein Science Last*, Ed. Coligan, John E., et al. (2010); *Current Protocols in Nucleic Acid Chemistry*, Ed. Egli, Martin (2010); *Current Protocols in Bioinformatics*, Ed. Baxevanis, Andreas D. (2010); and *Molecular Cloning: A Laboratory Manual*, Third Edition, Sambrook, Joseph (2001), all of which are incorporated herein by reference in their entirety.

In certain embodiments, when measuring biomarkers or other indicators of treatment, an "increased" or "decreased" amount or level may include a "statistically significant" amount. A result is typically referred to as statistically significant if it is unlikely to have occurred by chance. The significance level of a test or result relates traditionally to the amount of evidence required to accept that an event is unlikely to have arisen by chance. In certain cases, statistical significance may be defined as the probability of making a decision to reject the null hypothesis when the null hypothesis is actually true (a decision known as a Type I error, or "false positive determination"). This decision is often made using the p-value: if the p-value is less than the significance level, then the null hypothesis is rejected. The smaller the p-value, the more significant the result. Bayes factors may also be utilized to determine statistical significance (see, e.g., Goodman S., *Ann Intern Med.* 130:1005-13, 1999). In some embodiments, an "increased" or "decreased" amount or level is about 1.1×, 1.2×, 1.3×, 1.4×, 1.5×, 2×, 2.5×, 3×, 3.5×, 4×, 4.5×, 5×, 6×, 7×, 8×, 9×, 10×, 15×, 20×, 25×, 30×, 40×, or 50× more or less the amount of a predetermined standard, or the amount of a determined time point relative to a previous or earlier timepoint.

Also provided are methods for monitoring the efficacy of an active agent in the treatment of cancer. These methods include determining the activity of one or more biomarkers of the present invention in a biological sample from a patient and providing that information regarding the biomarkers to an entity that provides a determination or evaluation of the treatment or efficacy based on biomarker information. In some embodiments, the biomarker activity is determined during or after taking at least one dosage of the active agent of the present invention. In some embodiments, the entity can provide a determination that treatment with the active agent should be used or should be continued, if the human subject meets one or more selection criteria described below:

The human subject has a decreased level of IL-1β activity when compared to that of the same human subject before the treatment, and/or has a normalization or stabilization of the IL-1β activity when compared that of a human subject or a group of human subjects who are responsive to a treatment of the present invention;

The human subject has an increased level of IL-4 activity when compared to that of the same human subject before the treatment, and/or has a normalization or stabilization of the IL-4 activity when compared that of a human subject or a group of human subjects who are responsive to a treatment of the present invention;

The human subject has a decreased level of IL-6 activity when compared to that of the same human subject before the treatment, and/or has a normalization or stabilization of the IL-1β activity when compared that of a human subject or a group of human subjects who are responsive to a treatment of the present invention;

The human subject has a decreased level of IL-10 activity when compared to that of the same human subject before the treatment, and/or has a normalization or stabilization of the IL-1β activity when compared that of a human subject or a group of human subjects who are responsive to a treatment of the present invention.

Methods for detecting the levels of nucleic acids, such as RNA or DNA have been well described and are well known to those of skill in the art. Methods for detecting RNA can include but are not limited to RT-PCR, northern blot analyses, gene expression analyses, microarray analyses, gene expression chip analyses, hybridization techniques (including FISH), expression beadchip arrays, and chromatography as well as any other techniques known in the art. Methods for detecting DNA can include but are not limited to PCR, real-time PCR, digital PCR, hybridization (including FISH), microarray analyses, SNP detection assays, SNP genotyping assays and chromatography as well as any other techniques known in the art.

Methods for detecting proteins and polypeptides can include but are not limited to spectrophotometric determination of protein concentration, quantitative amino acid analysis, protein concentration assays, chromatography assays, western blot analyses, gel electrophoresis, (followed by staining procedures including but not limited to Coomassie Blue, Silver stain, Syber Green, Syber Gold), hybridization, multiplex cytokine assays, immunoassays, ELISA, bicinchoninic acid (BCA) protein assays, Bradford protein assays, and Lowry protein assays as well as any other techniques known in the art. Protein detection can also include detecting the levels of stable or active proteins and methods such as kinetic assays, kinase assays, enzyme assays and post-translation modification assays (for example, assays for determining phosphorylation and glycosylation state) can also be employed.

For more methods related to detection, quantitation and comparison of biomarker levels, see, e.g., Current Protocols in Molecular Biology, Ed. Ausubel, Frederick M. (2010); Current Protocols in Protein Science Last, Ed. Coligan, John E., et al. (2010); Current Protocols in Nucleic Acid Chemistry, Ed. Egli, Martin (2010); Current Protocols in Bioinformatics, Ed. Baxevanis, Andreas D. (2010); and Molecular Cloning: A Laboratory Manual, Third Edition, Sambrook, Joseph (2001), all of which are incorporated herein by reference in their entireties.

In some embodiments, the information regarding the biomarkers is obtained from one or more tests. The test can be performed by the subject himself/herself, by a doctor, by a nurse, by a test lab, by a healthcare provider, or any other parties capable of doing the test. The test results containing the biomarker information can be then analyzed by the same party or by a second party, such as the subject himself/herself, a doctor, a nurse, a test lab, a healthcare provider, a physician, a clinical trial personnel, a hospital, a lab, a research institute, or any other parties capable of analyzing the test to determine if the subject is responsive to the drug.

The following examples illustrate various aspects of the invention. The examples should, of course, be understood to be merely illustrative of only certain embodiments of the invention and not to constitute limitations upon the scope of the invention.

EXAMPLES

Example 1

Treating Melanoma by Thymosin in Subcutaneous B16F10 Murine Melanoma Model

B16F10 murine melanoma model is derived from MB16 line by successive selection of metastatic clones. B16F1 to B16F10 (ATCC Number CRL6475™) were generated, with F10 being passaged in mice for 10 times, and thus highly metastatic. This model is widely used in studying metastasis mechanisms, evaluating cancer therapeutics. It is also one of the most common syngeneic models for cancer immunotherapy. Both subcutaneous and experimental metastasis models are very useful.

To study the effect of thymosin in treating melanoma, thymosin alpha peptide (ZADAXIN) was administered to mice inoculated with B16F10 in two separate studies:

TABLE 1

Study No. 1 Design

| Group | Treatment | Dose (mg/kg) | Notes |
|---|---|---|---|
| 1 | Vehicle | — | Vehicle or Ta1 |
| 2 | TA1 | 0.2 | given bid i.p. for 7 days |
| 3 | TA1 | 2 | after tumors reached 83-96 mm$^3$ |
| 4 | TA1 | 6 | Blood & serum collected for biomarker analysis at each time point (0, +2, +4 and +7) (n = 12 sacrificed at timepoints 1, +2 and_4 and 24 animals sacrificed at +7 for biomarker analysis) All biomarker analysis animals were also measured for tumor size prior to sacrifice at each timepoint to generate additional tumor size data Antitumor activity evaluated (n = 6 measured for tumor size at each timepoint, then sacrificed at end of study). Data from all animals measured or tumor size is depicted in the figures and tables and statistical analyses. |

TABLE 2

Study No. 2 Design

| Group | Treatment | Dose (mg/kg) | Route | Notes |
|---|---|---|---|---|
| 1 | Vehicle | — | s.c. | Vehicle or Ta1 |
| 2 | TA1 | 0.02 | s.c. | given bid i.p or s.c. depending upon |
| 3 | TA1 | 0.06 | s.c. | the dose group, for 7 days after |
| 4 | TA1 | 0.2 | i.p. | tumors reached 120 mm$^3$ |
| 5 | TA1 | 0.2 | s.c. | Blood & serum collected for |
| 6 | TA1 | 0.6 | s.c. | biomarker analysis at each time |
| 7 | TA1 | 2 | s.c. | point (n = 4 animals at 0, +2, +4 |
| 8 | TA1 | 6 | s.c. | and +7) All biomarker analysis animals were also measured for tumor size prior to sacrifice at each timepoint to generate additional tumor size data |

TABLE 2-continued

Study No. 2 Design

| Group | Treatment | Dose (mg/kg) | Route | Notes |
|---|---|---|---|---|
| | | | | Antitumor activity evaluated (n = 10 measured for tumor size at each timepoint, then sacrificed at end of study). Data from all animals measured or tumor size is depicted in the figures and tables and statistical analyses. |

Tumor volumes and body weights were monitored throughout the study. Cisplatin was administered to the positive control group in a separate historical control study. The negative control group was administered with vehicle only in all studies.

Figure 1B:
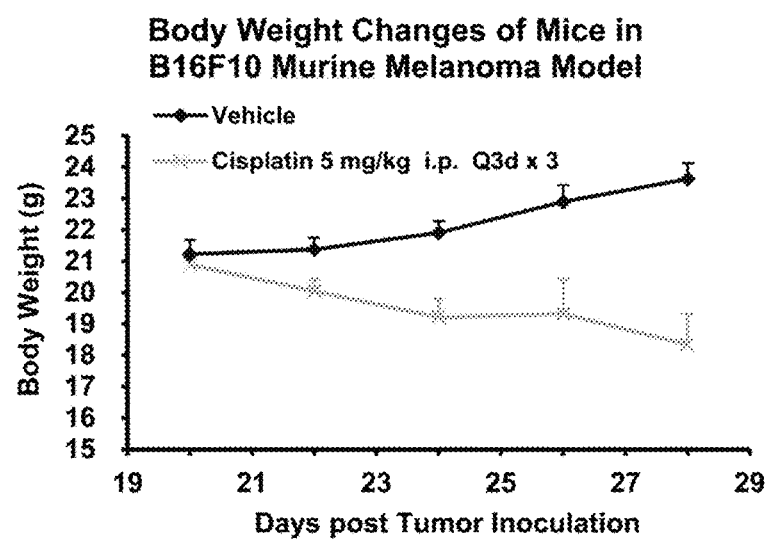
FIG. 1B depicts body weight changes of mice in B16F10 murine melanoma model post tumor inoculation treated with either vehicle or cisplatin.

B16F10 mice treated with cisplatin typically show reduced tumor volume (FIG. 1A and Table 3). However, these mice also had significantly reduced body weight as a result of the toxicity of cisplatin (FIG. 1B).

TABLE 3

Tumor size in B16F10 mice treated with cisplatin

| Treatment | Tumor Size (mm$^3$) on Day 28 | T/C Value (%) on Day 28 | T-C (days) at 800 mm$^3$ | P value |
|---|---|---|---|---|
| Vehicle | 2904 ± 538 | — | — | — |
| Cisplatin | 862 ± 233 | 30 | >4 | 0.006 |

Figure 2:
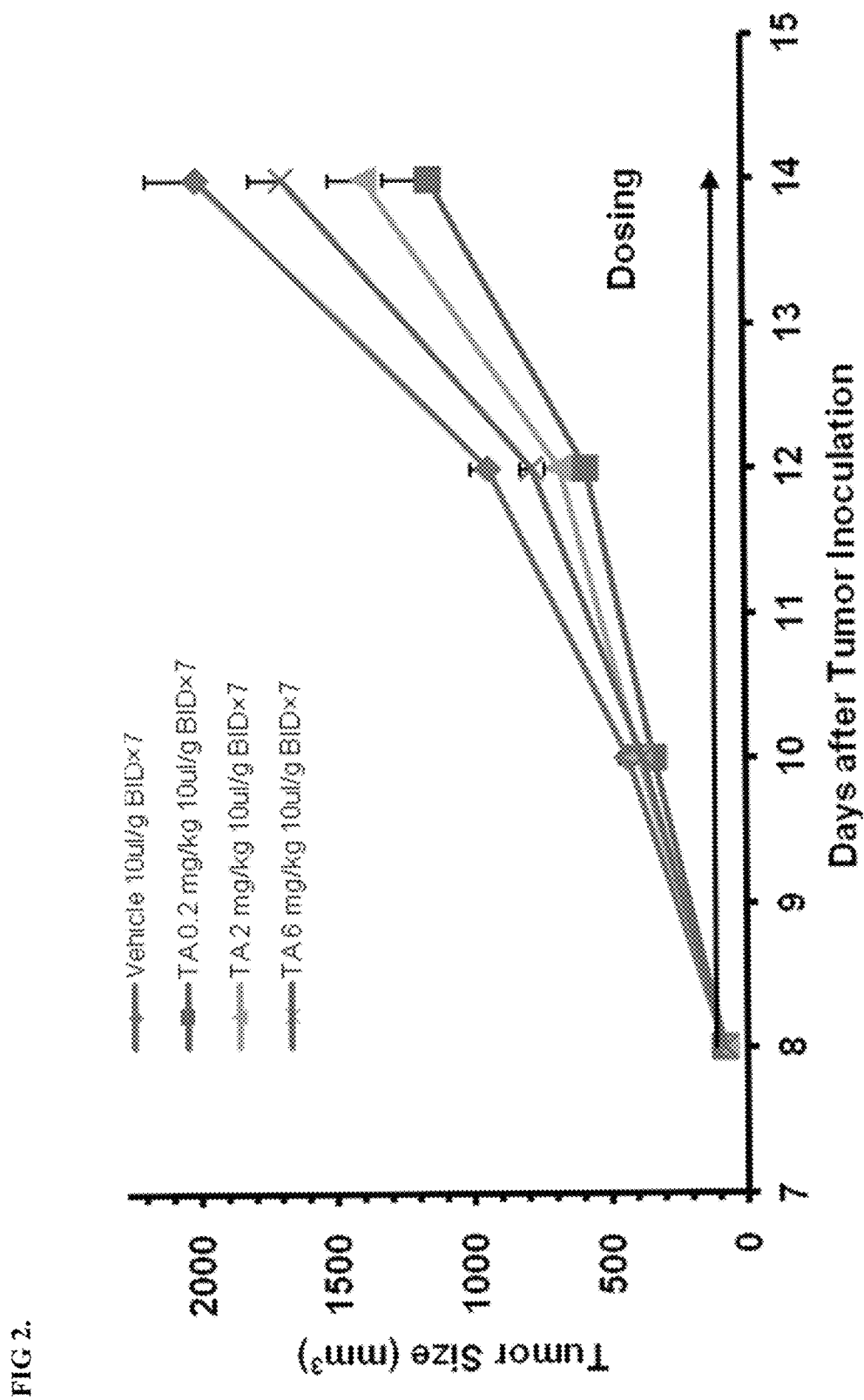
FIG. 2 depicts antitumor activity of thymosin. Animals with B16F10 derived tumor were treated with ZADAXIN™ (thymalfasin). At all doses tested, animals exhibited reduced tumor growth compared with vehicle treated group.
Figure 3:
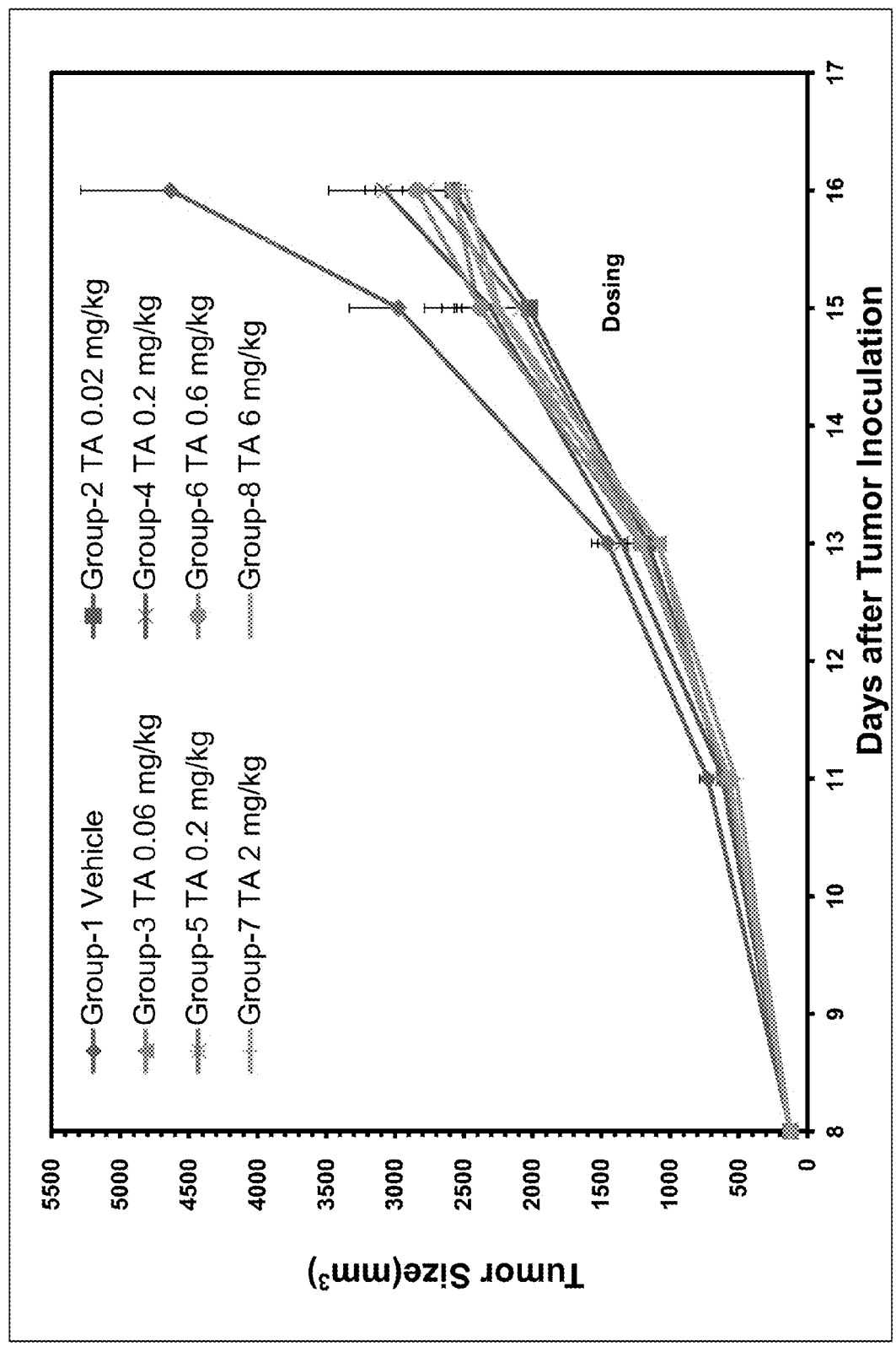
FIG. 3 depicts antitumor activity of thymosin at several different doses. At all tested doses, thymosin provided statistically significant reduced tumor growth compared with vehicle treated group.
Figure 4A:
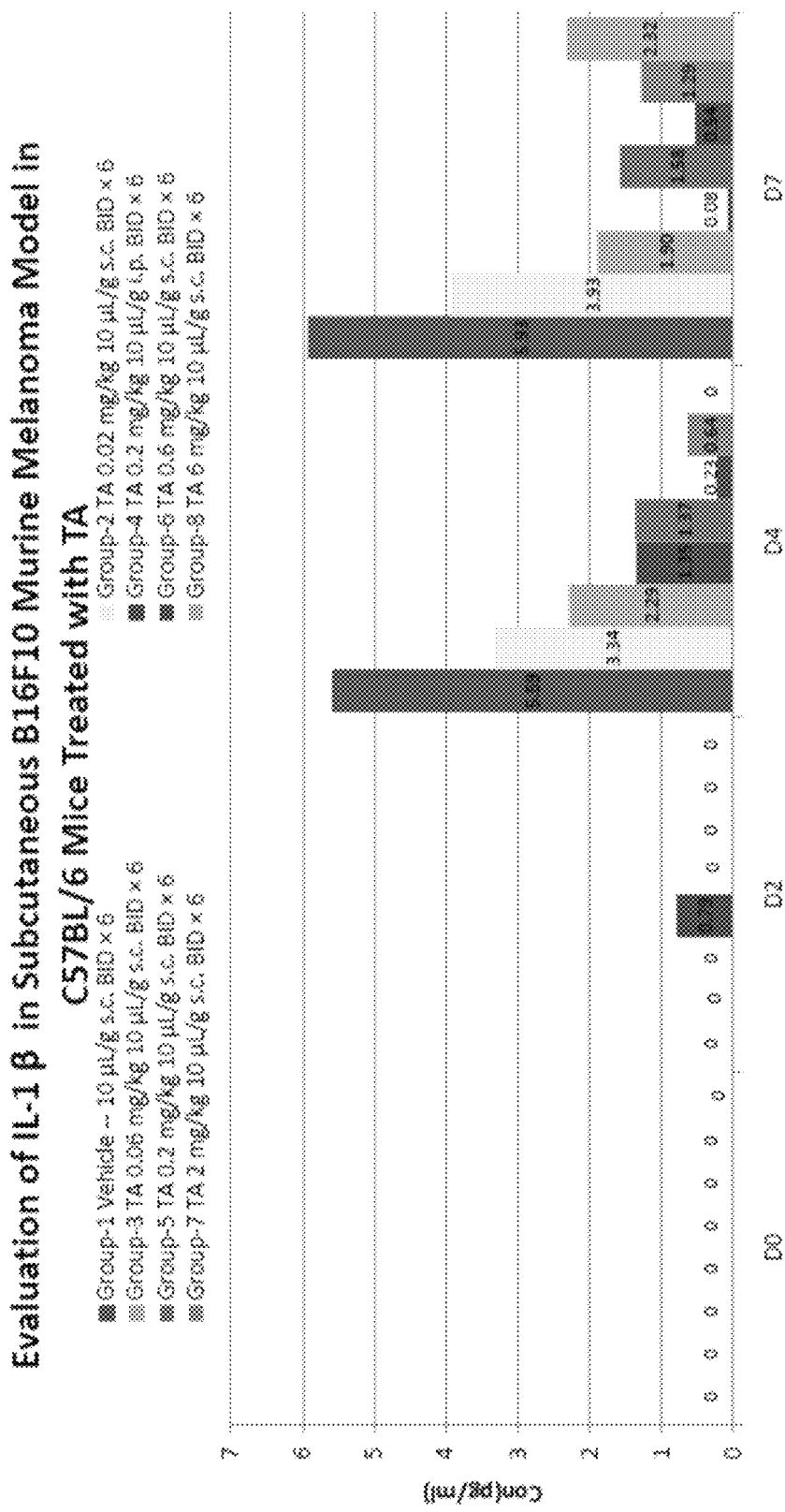
FIG. 4A depicts evaluation of IL-1β in subcutaneous B16F10 murine melanoma model in C57BL/6 mice treated with thymosin. ZADAXIN™ (thymalfasin) was administered to mice subcutaneously twice a day for 6 days at 0.02, 0.06, 0.2, 0.3, 2, or 6 mg/kg 10 μL/g. IL-1β levels were lower in ZADAXIN™ (thymalfasin) treated groups compared to vehicle treated groups at D4 and D7 after start of dosing.
Figure 4B:
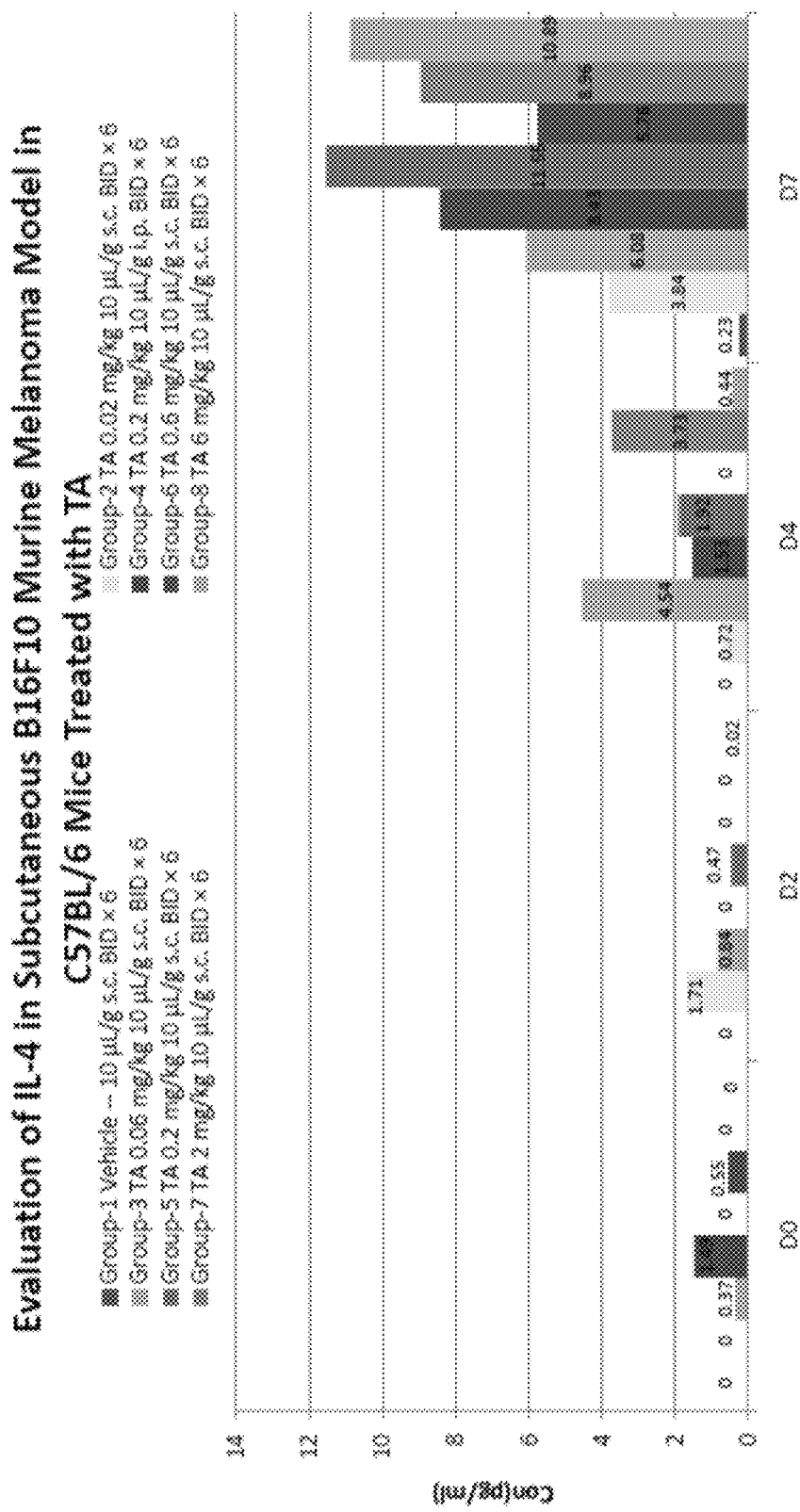
FIG. 4B depicts evaluation of IL-4 in subcutaneous B16F10 murine melanoma model in C57BL/6 mice treated with thymosin. ZADAXIN™ (thymalfasin) was administered to mice subcutaneously twice a day for 6 days at 0.02, 0.06, 0.2, 0.3, 2, or 6 mg/kg 10 μL/g. IL-4 levels were higher in ZADAXIN™ (thymalfasin) treated groups compared to vehicle treated groups at D4 and D7 after start of dosing.
Figure 4C:
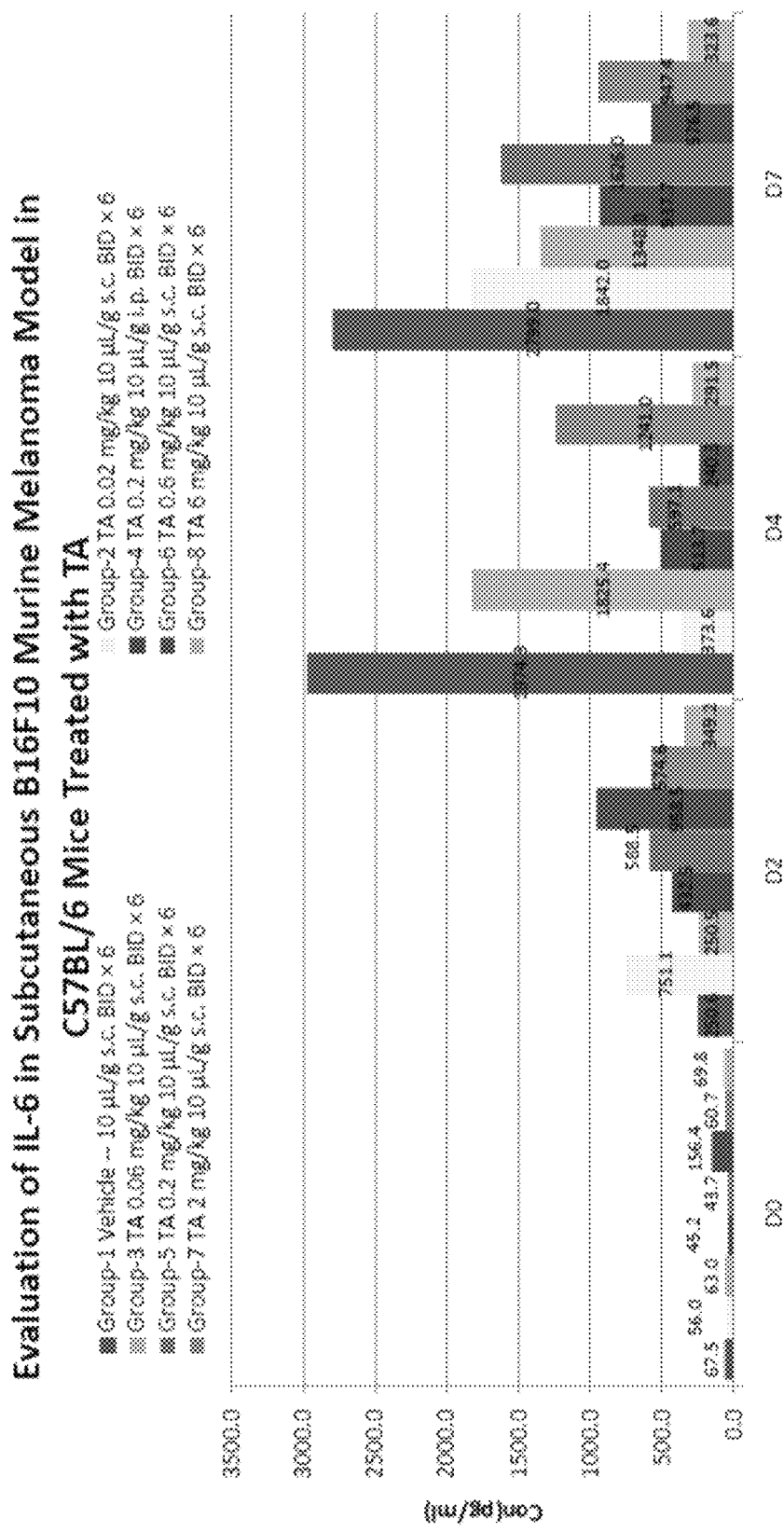
FIG. 4C depicts evaluation of IL-6 in subcutaneous B16F10 murine melanoma model in C57BL/6 mice treated with thymosin. ZADAXIN™ (thymalfasin) was administered to mice subcutaneously twice a day for 6 days at 0.02, 0.06, 0.2, 0.3, 2, or 6 mg/kg 10 μL/g. IL-6 levels were lower in ZADAXIN™ (thymalfasin) treated groups compared to vehicle treated groups at D4 and D7 after start of dosing.
Figure 4D:
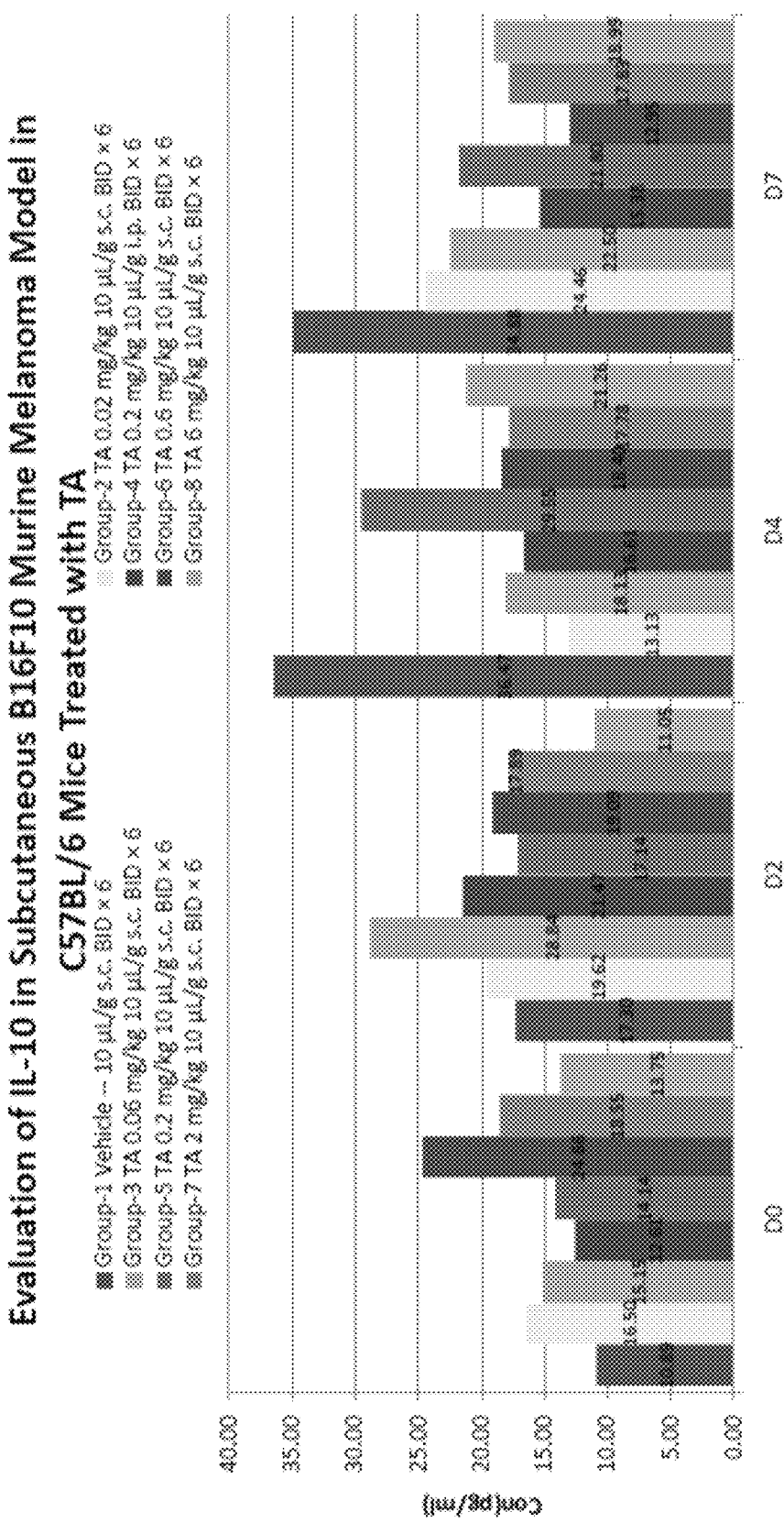
FIG. 4D depicts evaluation of IL-10 in subcutaneous B16F10 murine melanoma model in C57BL/6 mice treated with thymosin. ZADAXIN™ (thymalfasin) was administered to mice subcutaneously twice a day for 6 days at 0.02, 0.06, 0.2, 0.3, 2, or 6 mg/kg 10 μL/g. IL-10 levels were lower in ZADAXIN™ (thymalfasin) treated groups compared to vehicle treated groups at D4 and D7 after start of dosing.
Figure 4E:
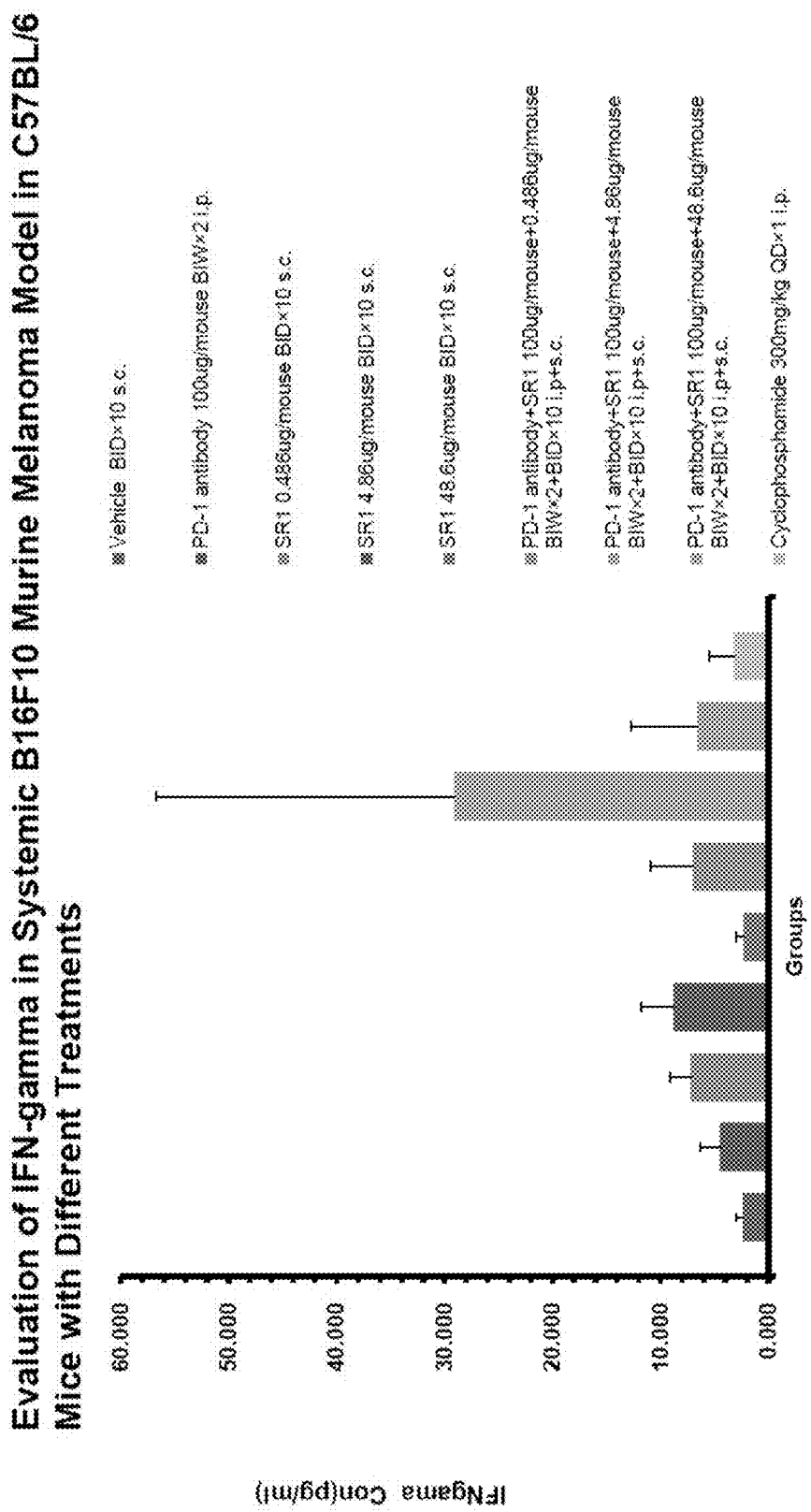
FIG. 4E depicts evaluation of IFN-gamma in systemic B16F10 murine melanoma model in C57BL/6 mice with different treatments.
Figure 4F:
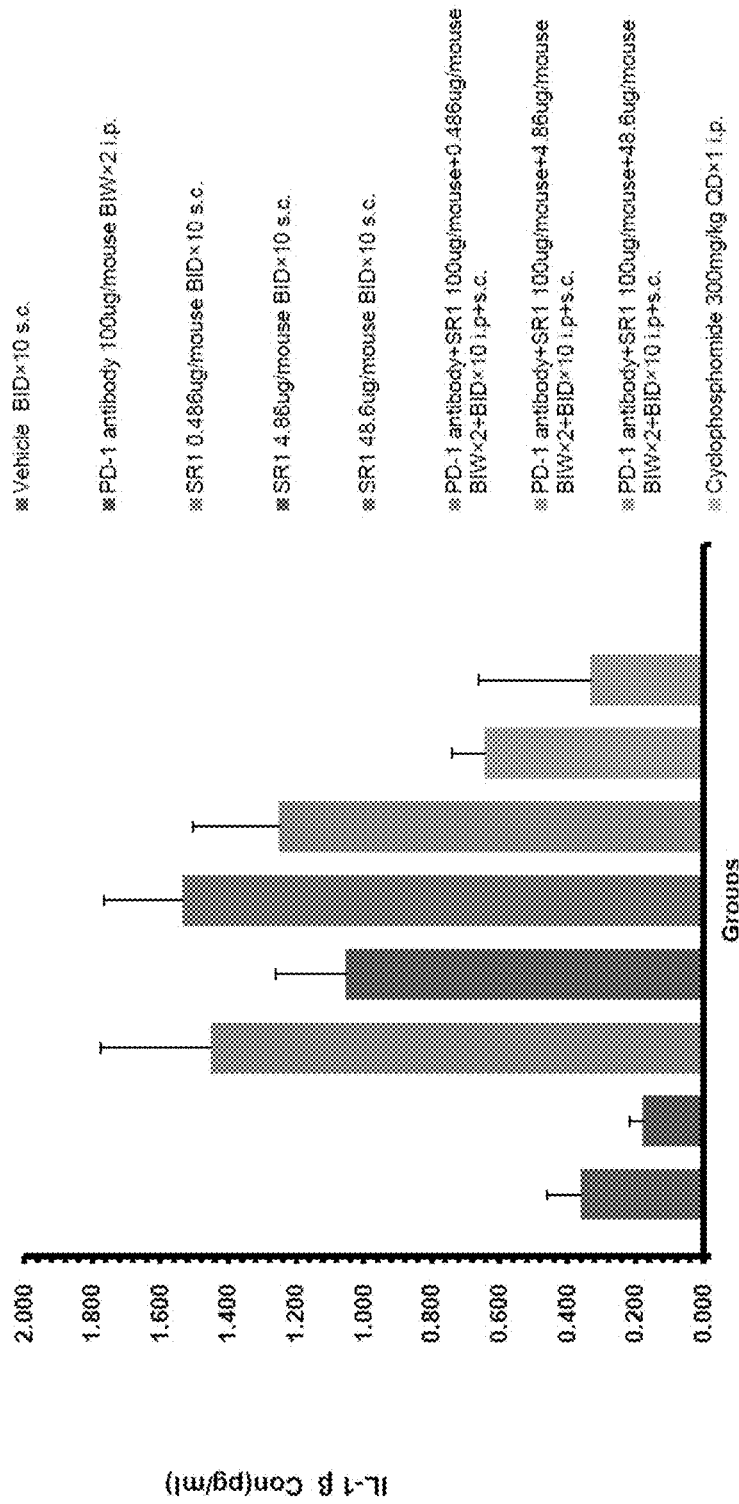
FIG. 4F depicts evaluation of IL-1β in systemic B16F10 murine melanoma model in C57BL/6 mice with different treatments.
Figure 4G:
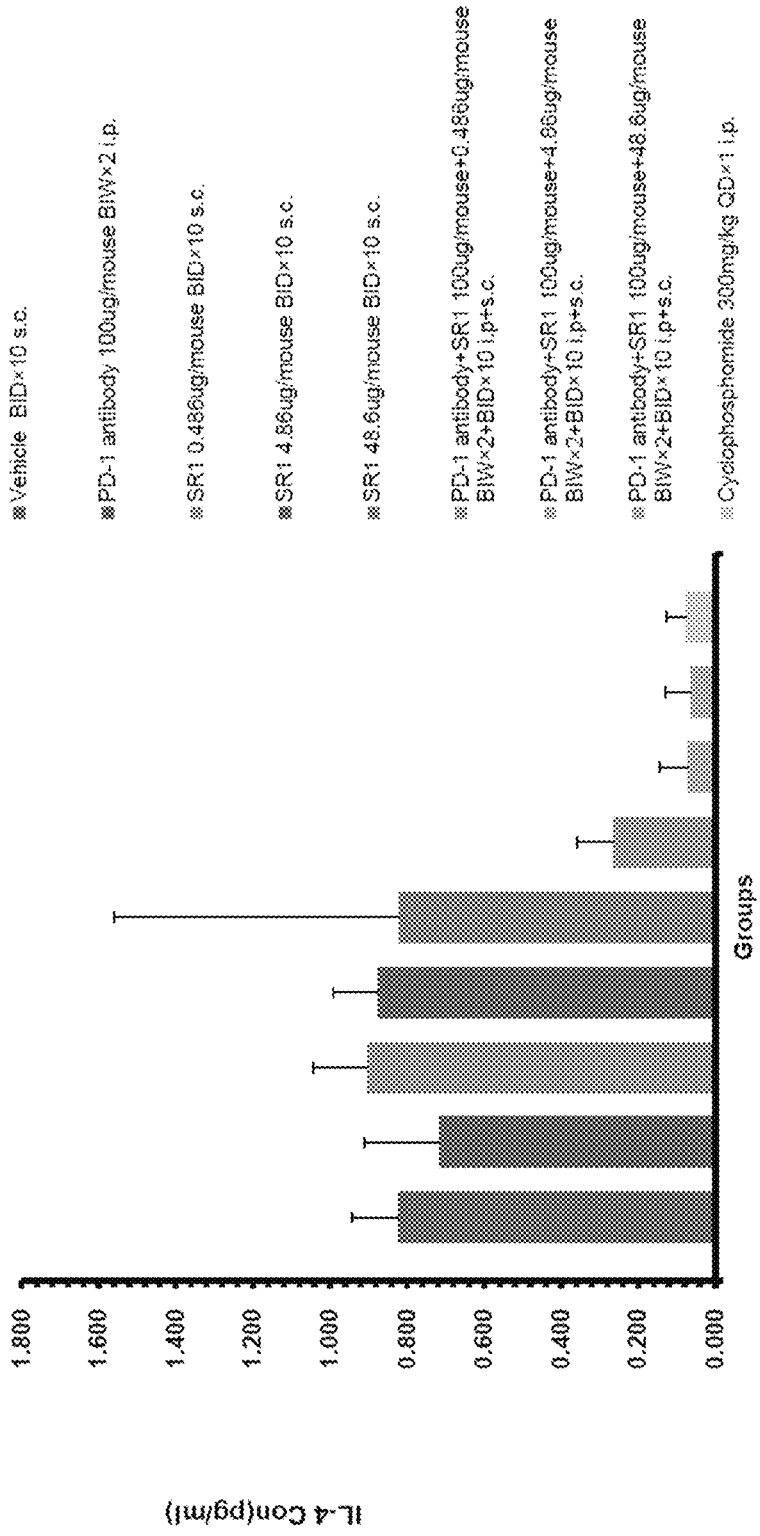
FIG. 4G depicts evaluation of IL-4 in systemic B16F10 murine melanoma model in C57BL/6 mice with different treatments.
Figure 4H:
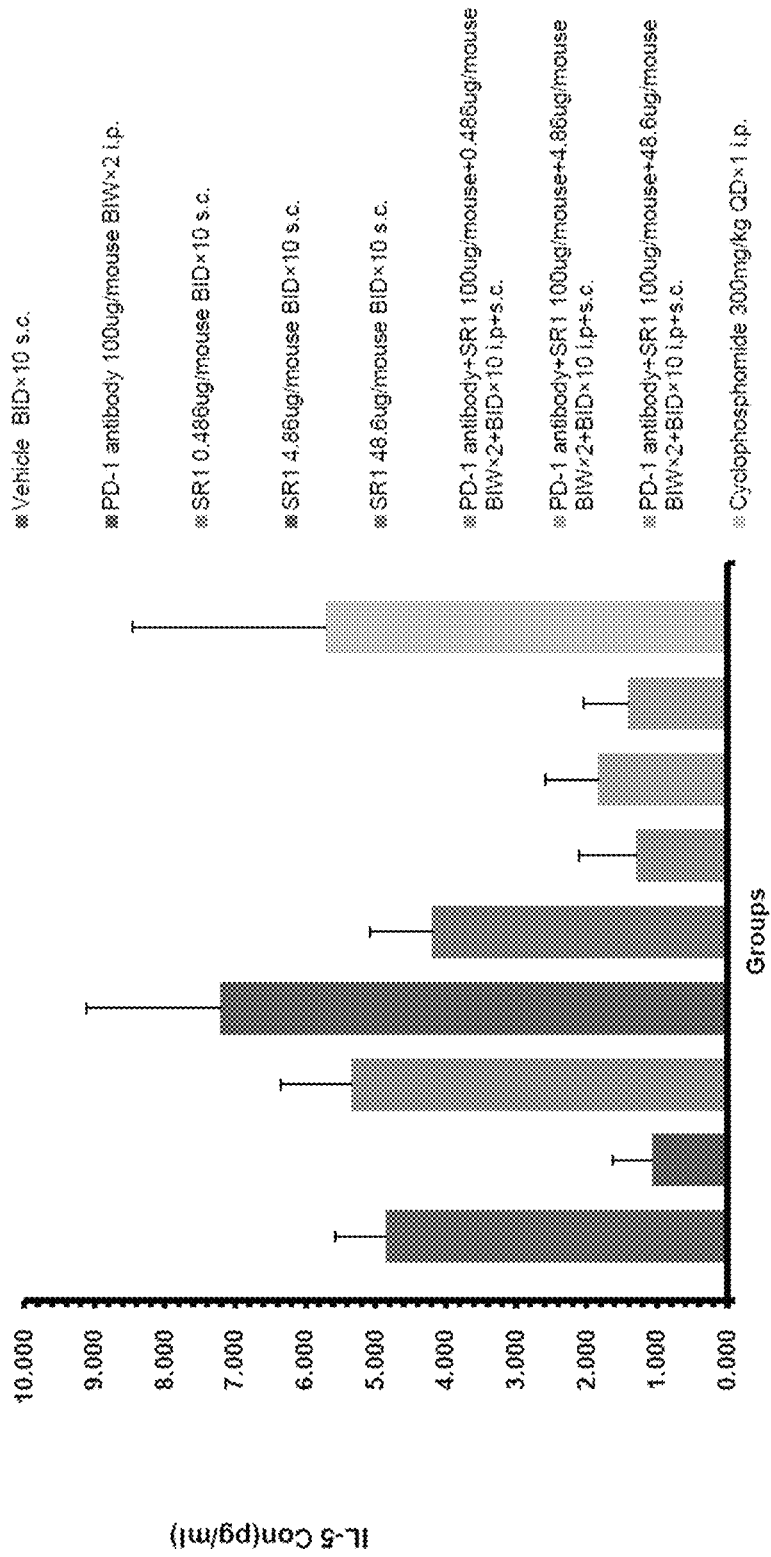
FIG. 4H depicts evaluation of IL-5 in systemic B16F10 murine melanoma model in C57BL/6 mice with different treatments.
Figure 4I:
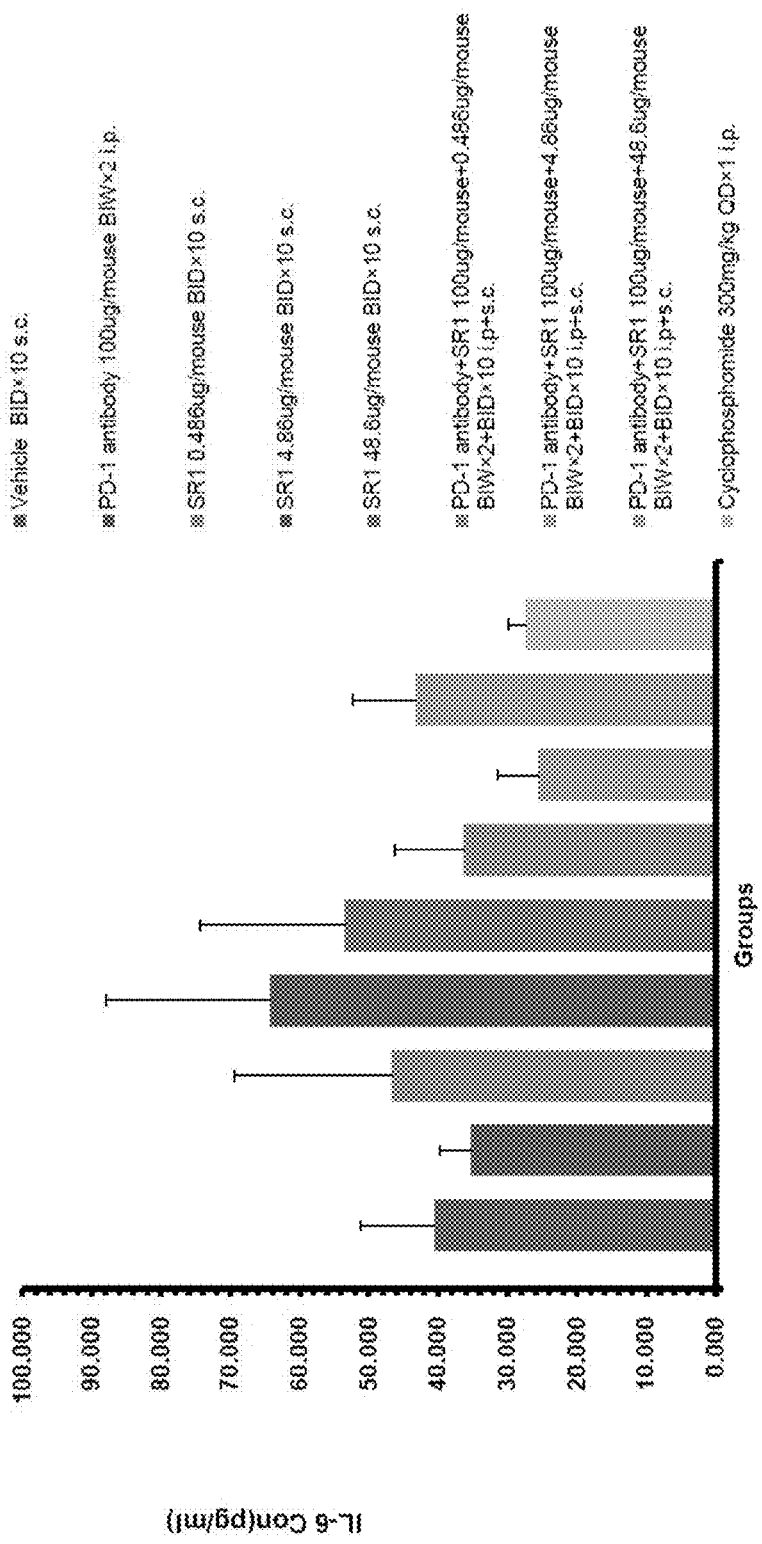
FIG. 4I depicts evaluation of IL-6 in systemic B16F10 murine melanoma model in C57BL/6 mice with different treatments.
Figure 4J:
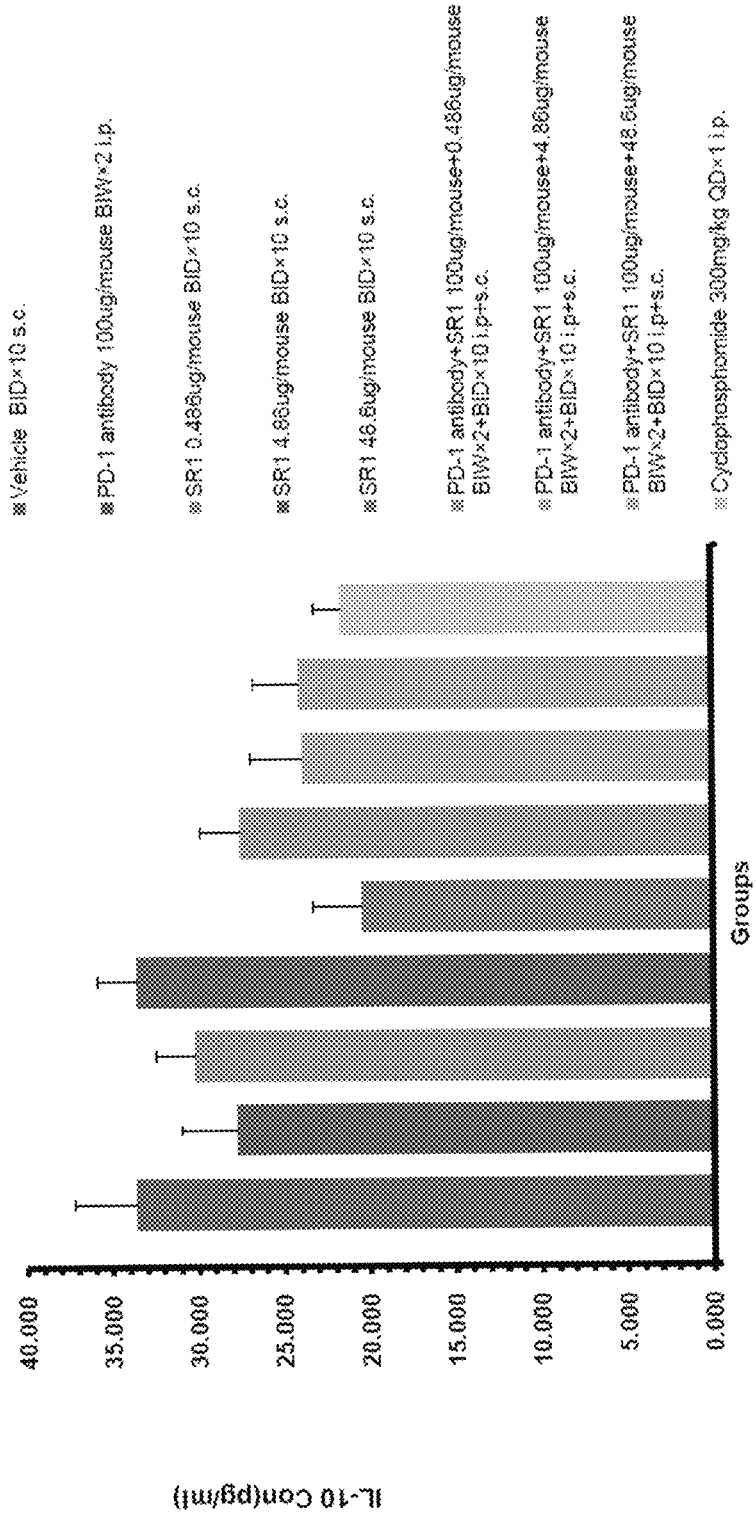
FIG. 4J depicts evaluation of IL-10 in systemic B16F10 murine melanoma model in C57BL/6 mice with different treatments.
Figure 4K:
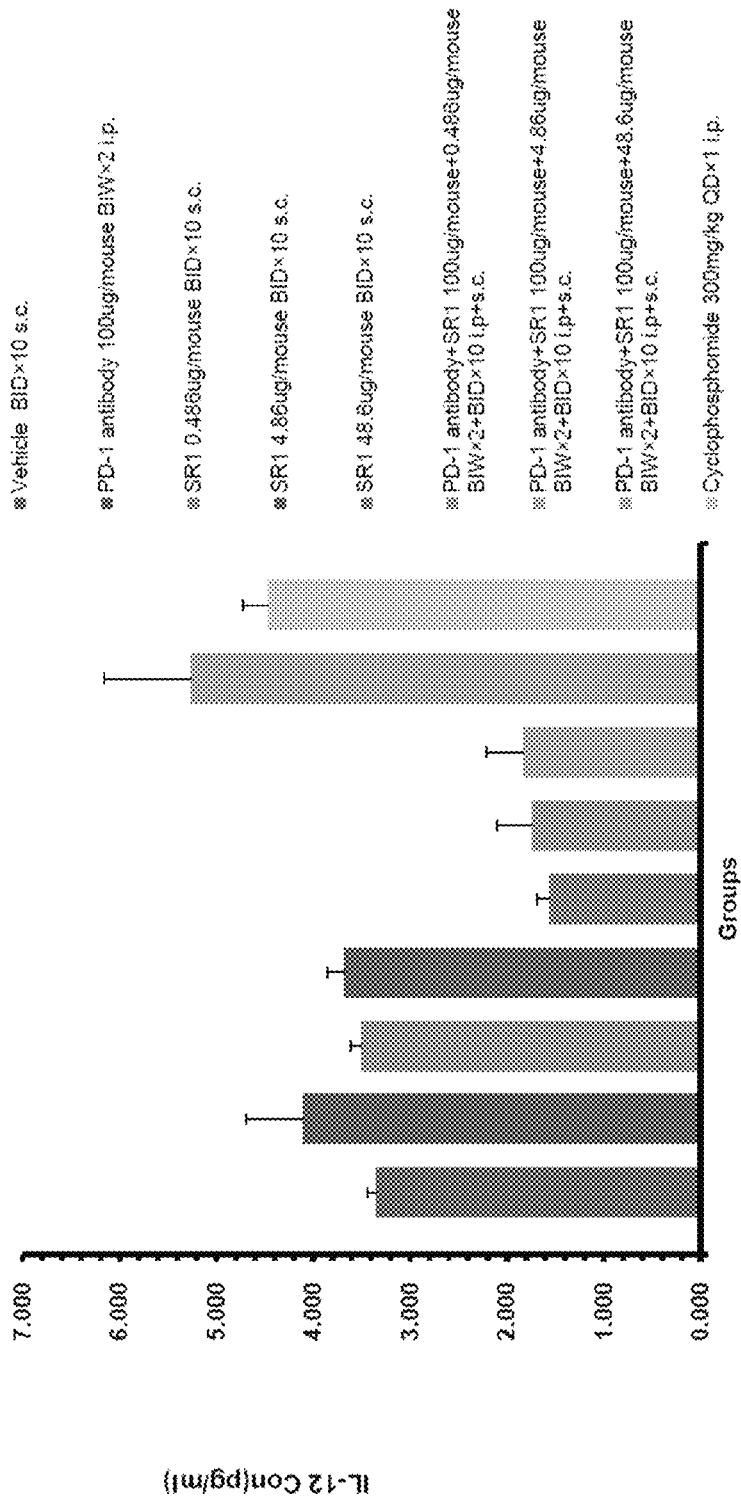
FIG. 4K depicts evaluation of IL-12 in systemic B16F10 murine melanoma model in C57BL/6 mice with different treatments.
Figure 4L:
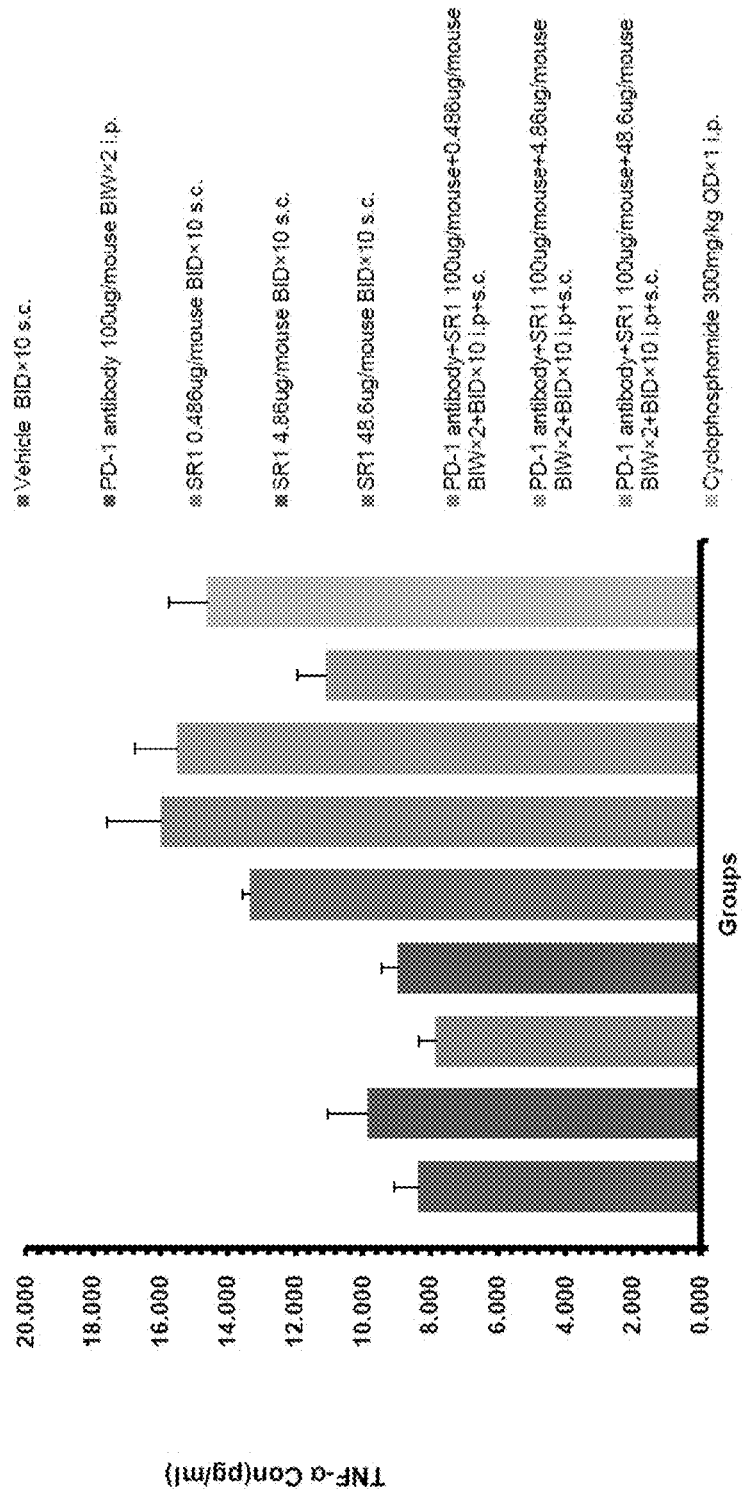
FIG. 4L depicts evaluation of TNF-α in systemic B16F10 murine melanoma model in C57BL/6 mice with different treatments.

Animals with B16F10 derived tumor, dosed with ZADAXIN™ (thymalfasin) at all doses tested exhibited reduced tumor growth compared with vehicle treated group (FIG. 2 and FIG. 3).

In study I, The mean tumor size of the vehicle treated group (Group1) reached 1,995 mm$^3$ at day 14 post tumor inoculation. Treatment with TA1 at 0.2 mg/kg and 2 mg/kg produced significant antitumor activity at day 14 post tumor inoculation. The mean tumor size was 1,148 mm3 (T/C value=57.56%, p value<0.001) and 1,384 mm$^3$ (T/C value=69.36%, p value=0.006) with a tumor growth delay of 1.5 and 0.5 day(s) respectively at tumor size of 1,140 mm$^3$. Treatment with TA1 at 6 mg/kg can delay tumor growth, but the decrease didn't reach a significant difference (p value=0.146). Moreover, TA1 at 0.2 mg/kg produced better antitumor activity than TA1 at 6 mg/kg.

In addition, no significant weight changes by group were observed. Therefore, thymosin can be used to treat melanoma.

Example 2

Biomarker Studies

In the studies described above, a group of potential biomarkers were tested in, including IL-7, 11-18, TREM-1, IFN-α, procalcitonin, GM-CSF, IL-1α, IFN-γ, TNF α, IL-2, IL-4, IL-5, IL-6, IL-10, IL-12p70, and IL-1β. The concentration of some particular biomarkers in mice treated by vehicle or ZADAXIN™ (thymalfasin) are shown in FIG. 4A to FIG. 4D. The results indicate that these biomarkers can be used to evaluate the efficacy of a cancer treatment (either a single agent or combination therapies), to select patients for effective treatment, and to optimize dose and/or regimen for either clinical studies or treatment.

In another study, 8 cytokines (IFNγ, IL-1β, IL-4, IL-5, IL-6, IL-10, IL-12, TNFα) in serum samples of systemic B16F10 murine melanoma model in C57BL/6 mice with different treatments were analyzed by ELISA. The treatments were:
1. Vehicle BID×10 s.c.
2. PD-1 antibody 100 ug/mouse biweek×2 i.p.
3. TA1 0.486 ug/mouse bid×10 s.c.
4. TA1 4.86 ug/mouse bid×10 s.c.
5. TA1 48.6 ug/mouse bid×10 s.c.
6. PD-1 antibody+TA1 (100 ug/mouse+0.486 ug/mouse; biweek×2+bid×10 i.p+s.c.)
7. PD-1 antibody+TA1 (100 ug/mouse+4.86 ug/mouse; biweek×2+bid×10 i.p+s.c.)
8. PD-1 antibody+TA1 (100 ug/mouse+48.6 ug/mouse; biweek×2+bid×10 i.p+s.c.)
9. Cyclophosphomide 300 mg/kg QD×1 i.p.

The concentration of these biomarkers in mice after treatment are shown in FIG. 4E to 4L. The results indicate that these biomarkers could be tied to mechanism of action of thymosin, or used as pharmacodynamic markers.

Example 3

Treating Melanoma by Thymosin in B16F10 Mouse Lung Metastatic Melanoma Model

Materials and Methods

Mice: Female B6D2F1/Crl mice (Charles River) were 9 weeks old on D1 of the study and had a BW range of 19.2 to 24.5 g. The animals were fed ad libitum water (reverse osmosis, 1 ppm Cl) and NIH 31 Modified and Irradiated Lab Diet® consisting of 18.0% crude protein, 5.0% crude fat, and 5.0% crude fiber. The mice were housed on irradiated Enrich-o'Cobs™ bedding in static microisolators on a 12-hour light cycle at 20-22° C. (68-72° F.) and 40-60% humidity. DRS-NC specifically complies with the recommendations of the Guide for Care and Use of Laboratory Animals with respect to restraint, husbandry, surgical procedures, feed and fluid regulation, and veterinary care. The animal care and use program at DRS-NC is accredited by the Association for Assessment and Accreditation of Laboratory Animal Care International, which assures compliance with accepted standards for the care and use of laboratory animals.

In Vivo Implantation: Test mice were sorted into five treatment groups (n=10), as shown in Table 1. A sixth group of animals was included as the "look-see" group (n=9). B16-F10 cells were harvested during log-phase growth and resuspended at a concentration of $7.5 \times 10^5$ cells/mL in PBS. Each mouse received an intravenous (i.v.) tail vein injection of $1.5 \times 10^5$ B16-F10 cells (0.2 mL cell suspension) on D1 of the study.

Test Articles: Anti-PD1 alpha peptide (coded as anti-PD-1-SCE, Lot. No. 5177/0214) and thymosin alpha-1 peptide (Thymalfasin, code-named SR1, Lot. No. 1402-224). DRS-NC assigned code names for the purpose of confidentiality during in-house testing. Cyclophosphamide (Baxter Pharmaceutical, Lot. No. 2E718F, received on Jun. 7, 2013) was included as a reference control. SR1 was provided as a lyophilized powder (90.7% free base) and was dissolved in PBS to yield a 22.051 mg/mL dosing solution, which provided a 220.51 mg/kg dosage in a dosing volume of 10 mL/kg. Dosing was not adjusted per body weight. Anti-PD-1-SCE antibody was diluted in PBS to yield a 10.0 mg/mL dosing solution, which provided a 100 mg/kg dosage in a dosing volume of 10 mL/kg. Dosing was not adjusted per body weight. Cyclophosphamide was diluted in saline to yield a 15.0 mg/mL dosing solution, which provided a 300 mg/kg dosage in a dosing volume of 15 mL/kg. Dosing was adjusted per body weight. Cyclophosphamide was prepared once at the beginning of the study and stored at 4° C.

Treatment: Table 4A presents a summary of the treatment plan:
Group 1 animals received PBS s.c. (bid to end) and served as the control treatment group.
Group 2 received SR1 s.c. at 220.51 mg/kg (200 mg/kg free base) (bid to end).
Group 3 received anti-PD-1-SCE administered i.p. at 100 mg/kg (biwk×3).
Group 4 received both SR1 and anti-PD-1-SCE administered at 220.51 mg/kg s.c. (bid to end) and 100 mg/kg i.p. (biwk×3) respectively.
Group 5 was set as the positive control group, and received cyclophosphamide at 300 mg/kg i.p. (qd×1),
Group 6 was set as the "look-see" animals and received no treatment.

Endpoint: The endpoint of the B16MET-e117 study was defined as 100 metastases per lung set. Two to three animals from the "look-see" group were euthanized in three days intervals beginning on Day 9 and lung metastatic foci were counted. Total counts were obtained by adding the number of foci counted in the superior, middle, inferior, and post-caval lobes of the right lung to the number of foci counted in the left lung. The study was terminated on D16 and all animals were euthanized and their metastases counted. Percent inhibition was defined as the difference between the number of metastatic foci of the designated control group and the number of metastatic foci of the drug-treated group, expressed as a percentage of the number of metastatic foci of the designated control group:

$$\% \text{ Inhibition} = [1-(\#\text{Foci drug-treated}/\#\text{Foci control})] \times 100$$

Toxicity: Animals were weighed daily for the first five days of the study and twice weekly thereafter. The mice were observed frequently for overt signs of any adverse, treatment-related side effects, and clinical signs of toxicity were recorded when observed. Acceptable toxicity was defined as a group mean body-weight loss of less than 20% during the study and not more than one treatment-related (TR) death among ten treated animals. Any dosing regimen resulting in greater toxicity is considered above the maximum tolerated dose (MTD). A death is classified as TR if attributable to treatment side effects as evidenced by clinical signs and/or necropsy, or if due to unknown causes during the dosing period or within fourteen days of the last dose. A death is classified as non-treatment-related (NTR) if there is no evidence that death was related to treatment side effects.

Statistical and Graphical Analyses: Prism (GraphPad) for Windows 6.02 was used for all graphical presentations and statistical analyses. The Mann-Whitney U-test, for analysis of medians, was used to determine the statistical significance between D16 B16F10 metastatic foci in control and treated groups. Two-tailed statistical analyses were conducted at P=0.05. A "box and whiskers" diagram was constructed to show the distribution of enumerated metastatic foci for each treatment group on D16.

Prism reports results as non-significant (ns) at $P>0.05$, significant (symbolized by "*") at $0.01<P\leq0.05$, very significant ("") at $0.001<P\leq0.01$, and extremely significant ("*") at $P\leq0.001$. Since the Mann-Whitney U-test is a test of significance and does not provide an estimate of the size of the difference between groups, all levels of significance are reported as either significant or non-significant in Table 4B.

Procedures:
Implant cells (1) day prior to study start.
Set up 59 CR female B6D2F1 mice with $1.5 \times 10^5$ B16MET tumor cells in 0% Matrigel iv tail vein.
Cell Injection Volume is 0.2 mL/mouse.
Age at Start Date: 8 to 12 weeks.
Body Weight: 5/2 then biweek to end
Met Count: at endpoint
Report any adverse reactions or death to RM, SD, RD or SH immediately.
Any individual animal with a single observation of >than 30% body weight loss or three consecutive measurements of >25% body weight loss will be euthanized.
Any group with a mean body weight loss of >20% or >10% mortality will stop dosing.
The group is not euthanized and recovery is allowed. Within a group with >20% weight loss, individuals hitting the individual body weight loss endpoint will be euthanized. If the group treatment related body weight loss is recovered to within 10% of the original weights, dosing may resume at a lower dose or less frequent dosing schedule. Exceptions to non-treatment body weight % recovery may be allowed on a case-by-case basis.
Endpoint: approximately 100 mets per lung set.
Euthanize moribund animals per CRL-NC SOP #687. Animals showing signs of respiratory distress will also be euthanized as stated above.

Tumor Cell Culture: B16MET cells were grown to mid-log phase in RPMI 1640 medium containing 10% fetal bovine serum, 10 mM HEPES, 2 mM glutamine, 100 units/mL sodium penicillin G, 0.075% sodium bicarbonate, 25 μg/mL gentamicin, and 100 μg/mL streptomycin sulfate. The tumor cells were cultured in tissue culture flasks in a humidified incubator at 37° C., in an atmosphere of 5% CO2 and 95% air.

B16F10 Mouse Lung Metastatic Melanoma Model was developed. About $1.5 \times 10^5$ B16-F10 cells (0.2 mL cell suspension) were grown in vitro and administered intravenously (Day 0) to female B6D2F1/Crl mice. On Day 1 dosing with test agents initiated.

Figure 5:
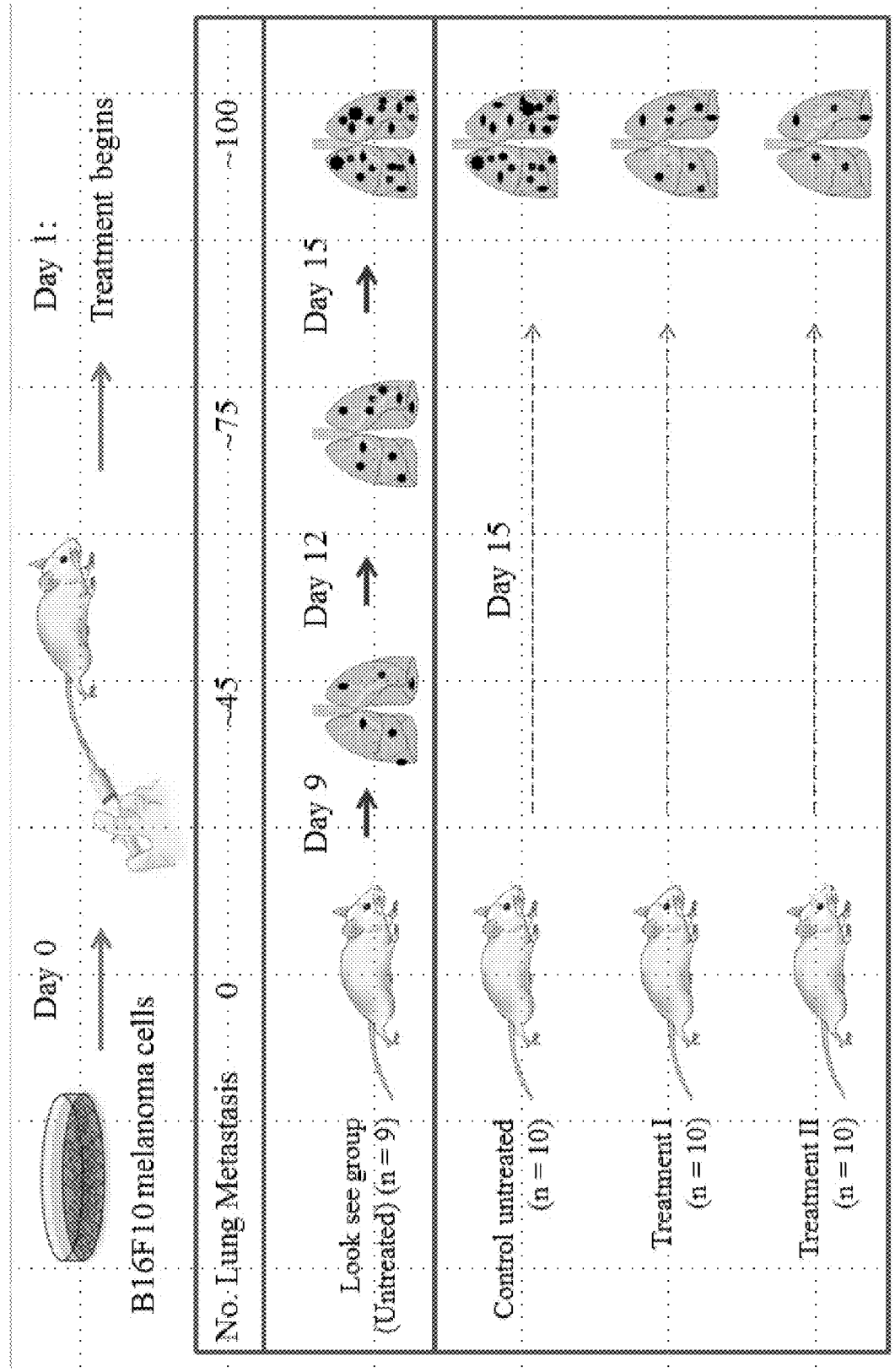
FIG. 5 depicts B16F10 mouse lung metastatic melanoma model and the experiment design. B16F10 melanoma cells were inoculated into mice at day 0.

A "look see"-untreated-group was set to evaluate, over a period of 15 days, the number of metastasis. On day 9, three animals from the "look see" group were euthanized and lung metastasis were count (our historical data indicates that at this time we would be able to find about >50 mets in the lung of untreated mice). Three days later other three mice were examined. When the met count reached approximately 50-100 counts, all groups in the study were sacrificed and final met counts were established. The "look see" group count was not included in the final efficacy analysis. 50-100 met count defined as the target number because most of the individual metastasis could be count easily and mets were less likely to merge with each other difficulty the counting. See FIG. 5.

Figure 6A:
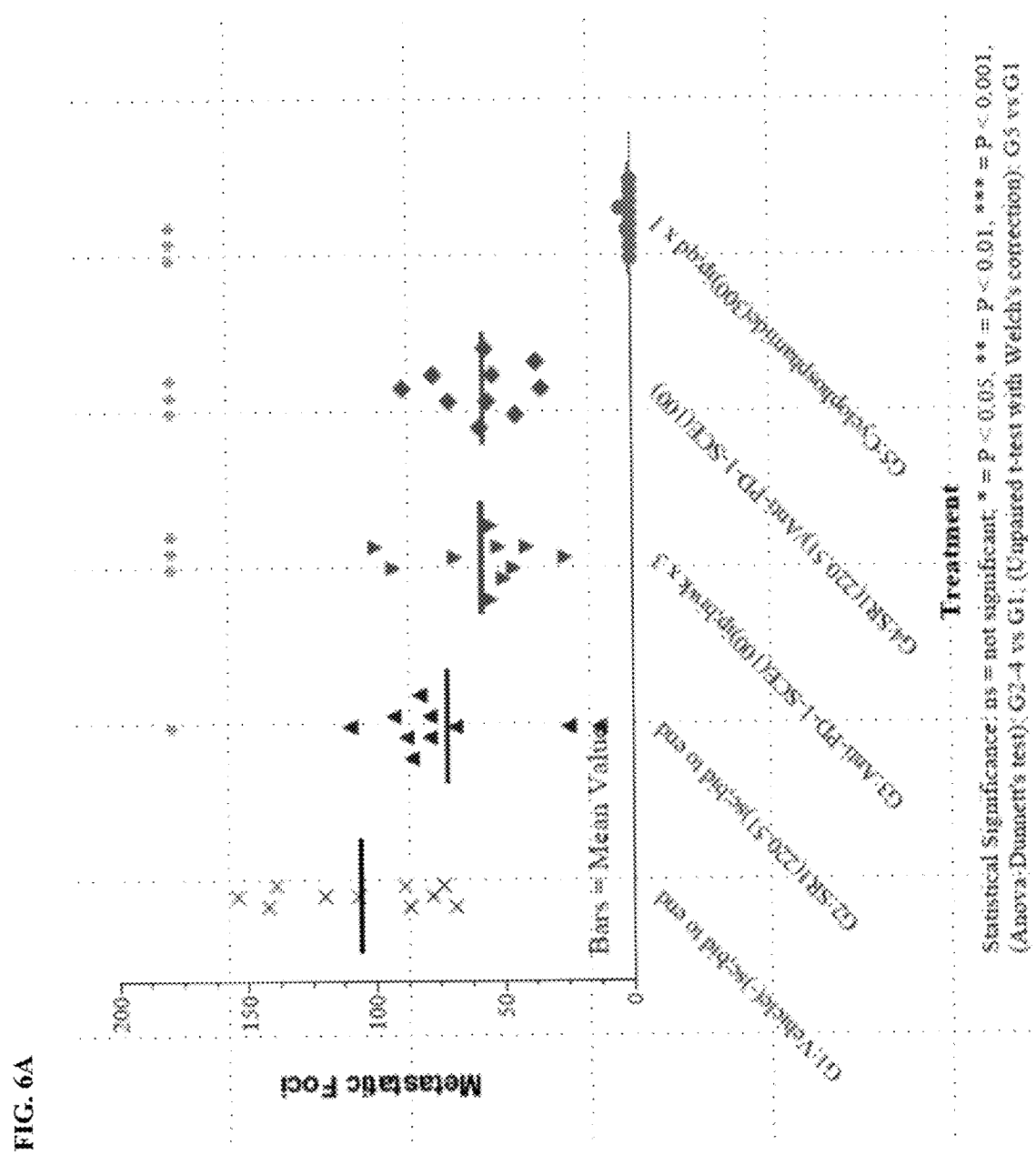
FIG. 6A depicts group distribution of lung metastases on day 16 in mice treated with vehicle, thymosin alone, anti-PD-1 alone, thymosin plus anti-PD-1, or cyclophosphamide.

In one study (Study I), vehicle (negative control), cyclophosphamide (positive control), TA1, anti-PD-1 or TA1+ anti-PD-1 was administered to mice, and met count was evaluated. The result is given in Table 4B below and in FIG. 6A and FIG. 6B.

TABLE 4A

Study 1 Design

| | | Treatment Regimen 1 | | | | Treatment Regimen 2 | | | |
|---|---|---|---|---|---|---|---|---|---|
| Group | n | Agent | Mg/kg | Route | Schedule | Agent | Mg/kg | Route | Schedule |
| 1 | 10 | Vehicle | — | sc | bid to end | — | — | — | — |
| 2 | 10 | SR1 | 220.51$^a$ | sc | bid to end | — | — | — | — |
| 3 | 10 | Anti-PD-1-SCE | 100$^a$ | ip | biwk x 2 | — | — | — | — |
| 4 | 10 | SR1 | 220.51$^a$ | sc | bid to end | Anti-PD-1-SCE | 100$^a$ | ip | biwk x 2 |
| 5 | 10 | Cyclophosphamide | 300 | ip | qd x 1 | — | — | — | — |
| 6 | 9 | LOOK SEE | — | iv | qd x 1 | — | — | — | — |

$^a$μg/animal

Vehicle = PBS

TABLE 4B

Study 1 Result

| | | Treatment Regimen | | | | Mean Met Count | SEM | n | Percent Inhibition | Statistical Significance | | Mean BW Nadir | Deaths | |
|---|---|---|---|---|---|---|---|---|---|---|---|---|---|---|
| Group | n | Agent | mg/kg | Route | Schedule | | | | | Vs G1 | Vs G4 | | TR | NTR |
| 1 | 10 | Vehicle | — | sc | bid to end | 105.9 | 9.8 | 10 | — | — | — | -2.1% Day 4 | 0 | 0 |
| 2 | 10 | SR1 | 220.51$^a$ | sc | bid to end | 72.5 | 9.6 | 10 | 31.5 | * | ns | — | 0 | 0 |
| 3 | 10 | Anti-PD-1-SCE | 100$^a$ | ip | biwk x 3 | 58.7 | 7.2 | 10 | 44.6 | *** | ns | — | 0 | 0 |
| 4 | 10 | SR1 Anti-PD-1-SCE | 220.51$^a$ 100$^a$ | sc ip | bid to end biwk x 3 | 58 | 5.4 | 10 | 45.2 | *** | — | — | 0 | 0 |

TABLE 4B-continued

Study 1 Result

| Group | n | Treatment Regimen | | | | Mean Met Count | SEM | n | Percent Inhibition | Statistical Significance | | Mean BW Nadir | Deaths | |
|---|---|---|---|---|---|---|---|---|---|---|---|---|---|---|
| | | Agent | mg/kg | Route | Schedule | | | | | Vs G1 | Vs G4 | | TR | NTR |
| 5 | 10 | Cyclophosphamide | 300 | ip | Qd x 1 | 0.5 | 0.4 | 10 | 99.5 | *** | — | −4.3% Day 3 | 0 | 0 |

$^a$μg/animal

Days in Progress = 16 n = number of animals in a group not dead from accidental causes (NTR deaths excluded from TGD calculations)

Percent Inhibition = [1 − (T/C)] × 100, compared to Group 1

Statistical Significance (ANOVA-Dunnett or Student's t -test):

ne = not evaluable, ns = not significant,

* = P < 0.05,

** = P < 0.01,

*** = P < 0.001, compared to group indicated

Mean BW Nadir = lowest group mean body weiaht, as % change from Day 1;

— indicates no decrease in mean body weight was observed

TR = treatment-related death;

NTR = non-treatment-related death

Figure 6B:
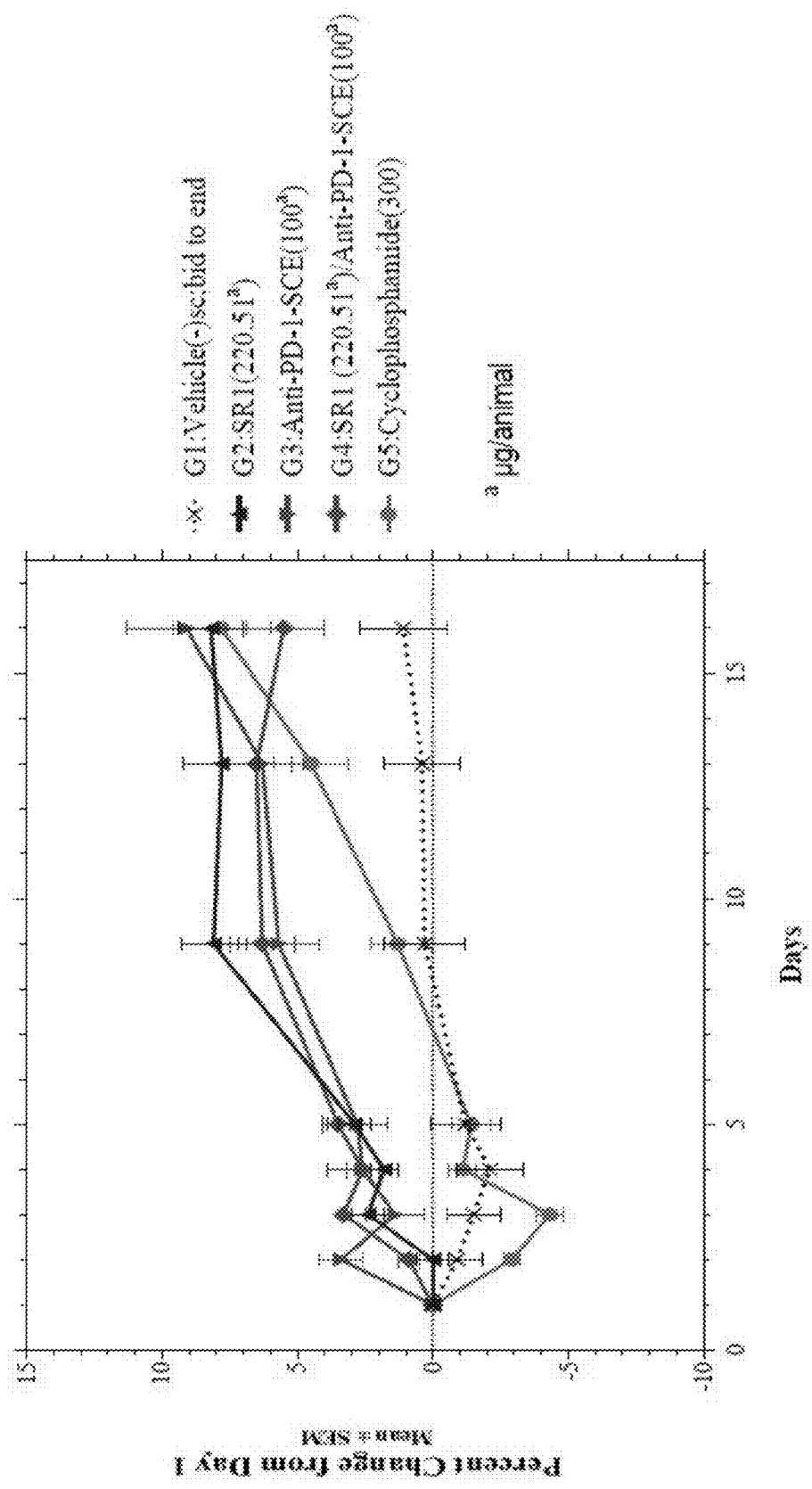
FIG. 6B depicts percent group mean body weight changes from Day 1 in B16MET mice treated with vehicle, thymosin alone, anti-PD-1 alone, thymosin plus anti-PD-1, or cyclophosphamide.

The percent group mean body weigh changes from Day 1 in B16MET-e117 mice are shown in FIG. 6B.

The result indicates that thymosin decreases metastases to lung in melanoma model, but there is no additive effect with anti-PD-1 at these particular doses.

Figure 7A:
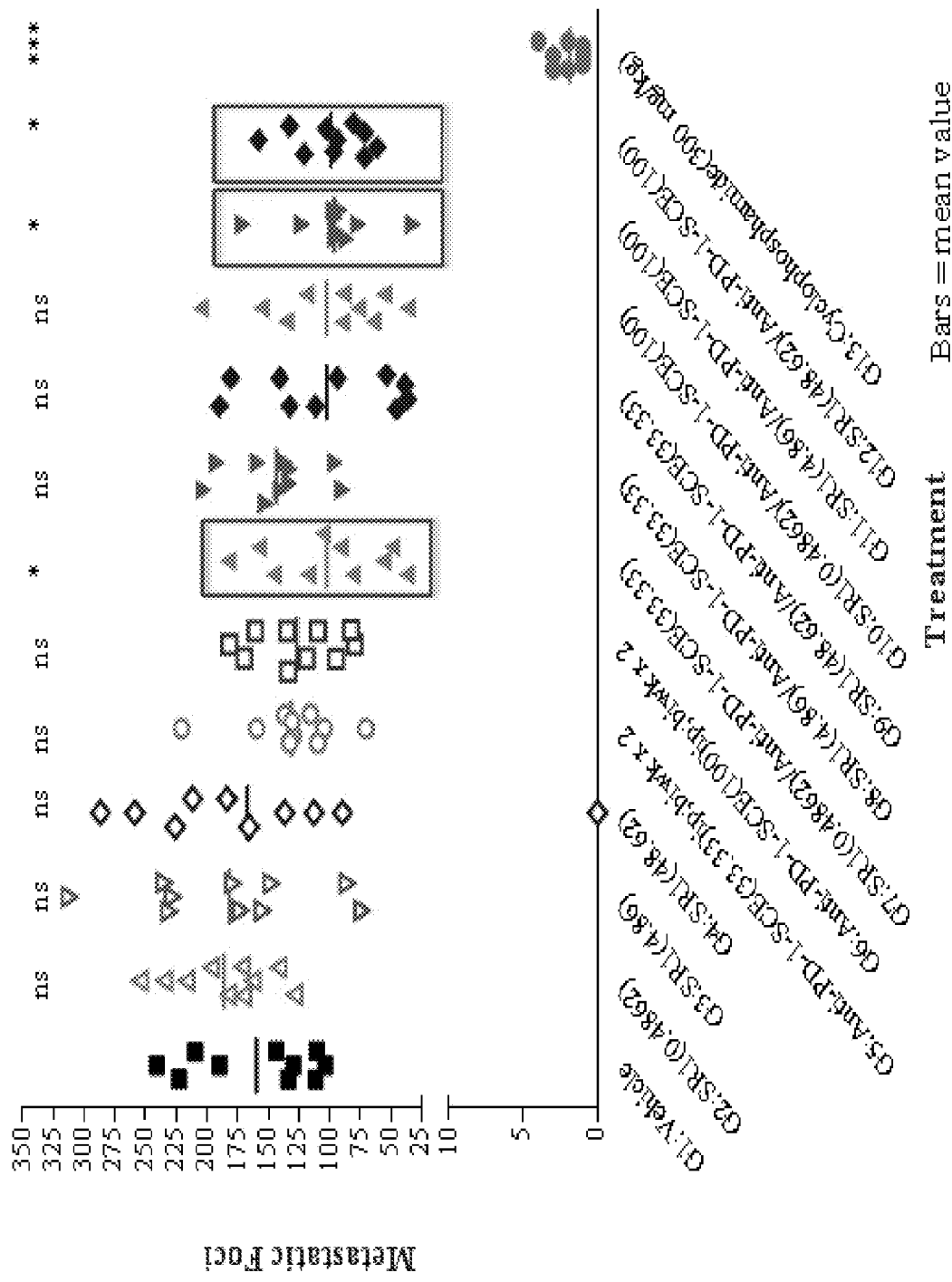
FIG. 7A depicts group distribution of lung metastases on day 15 in mice treated with vehicle, thymosin alone, anti-PD-1 alone, thymosin plus anti-PD-1, or cyclophosphamide at different doses.
Figure 7B:
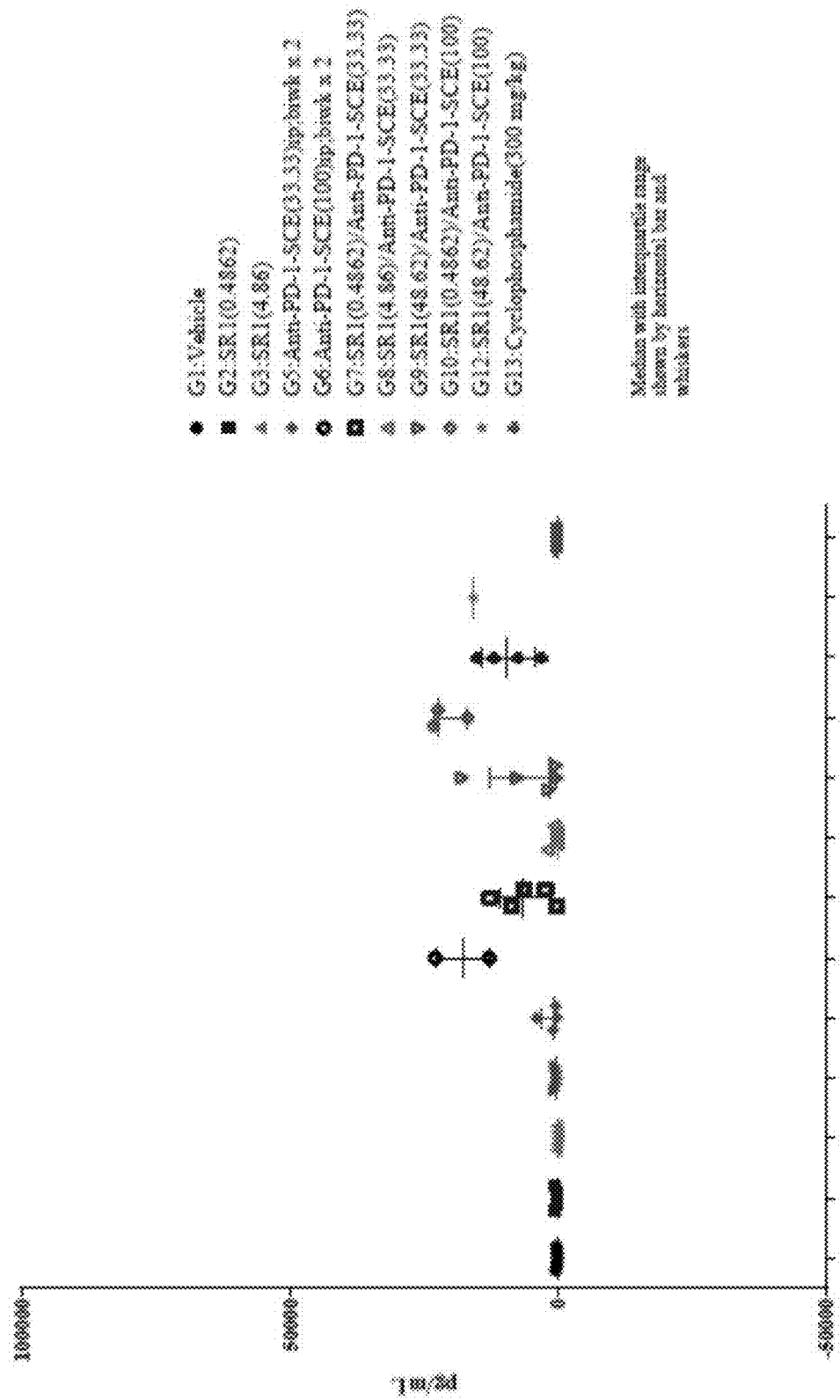
FIG. 7B depicts IL-1α in B16F10 mouse lung metastatic melanoma model after treatment with vehicle, thymosin alone, anti-PD-1 alone, thymosin plus anti-PD-1, or cyclophosphamide at different doses.
Figure 7C:
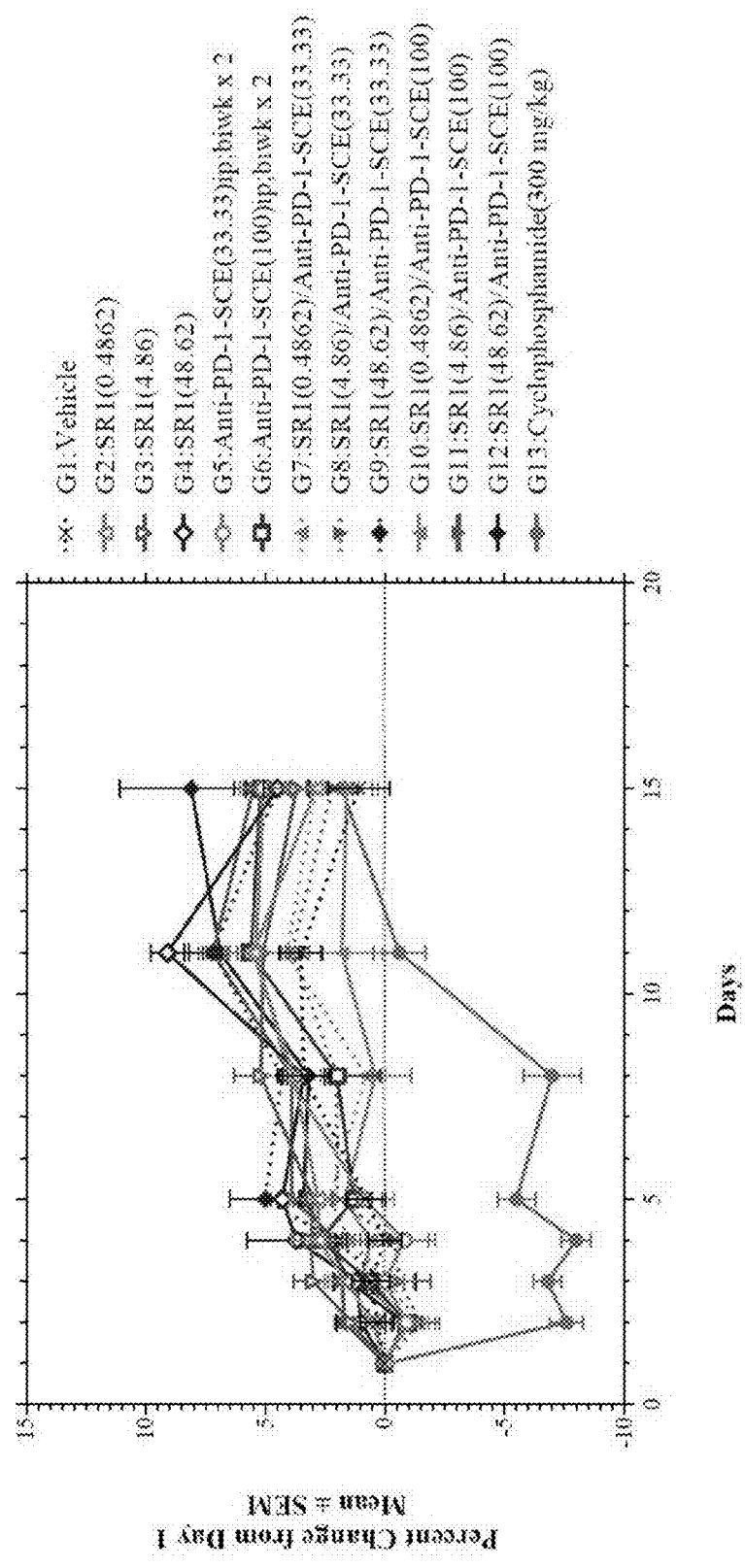
FIG. 7C depicts percent group mean body weight changes from Day 1 in B16F10 mice treated with vehicle, thymosin alone, anti-PD-1 alone, thymosin plus anti-PD-1, or cyclophosphamide.

In a second study (Study II), vehicle (negative control), cyclophosphamide (positive control), TA1, anti-PD-1 or TA1+anti-PD-1 was administered to mice at different doses. The study design and result are given in Table 5A and Table 5B below and in FIG. 7A to FIG. 7C.

Treatment Plan for Study II: In this study, thirteen groups of female B6D2F1 mice were dosed in accordance with the protocol in Table 5A. The SR1 and the vehicle were each administered subcutaneously (s.c.) twice daily for the duration of the study (bid to end). The anti-PD1 antibody was administered intraperitoneally (i.p.) twice a week for two weeks (biwk×2). A single dose of cyclophosphamide was administered i.p. (qd×1). Table 5A presents a summary of the treatment plan.

Group 1 animals received PBS and served as the control treatment group.

Groups 2-4 received SR1 at 0.4862, 4.862 and 48.62 μg/mouse (0.441, 4.41 and 44.1 μg/mouse free base), respectively.

Groups 5 and 6 received anti-PD-1 administered at 33.33 and 100 μg/mouse, respectively.

Groups 7-9 received SR1 at 0.4862, 4.862 and 48.62 μg/mouse in combination with anti-PD-1 administered at 33 μg/mouse, respectively Groups 10-12 received SR1 at 0.4862, 4.862 and 48.62 μg/mouse in combination with anti-PD-1 administered at 100 μg/mouse, respectively Group 13 was set as the positive control group, and received cyclophosphamide at 300 mg/kg.

Group 14 was set as the "look-see" animals and received no treatment.

TABLE 5A

Study II Design

| Group | n | Regimen 1 | | | | Regimen 2 | | | |
|---|---|---|---|---|---|---|---|---|---|
| | | Agent | μg/animal | Route | Schedule | Agent | Mg/kg | Route | Schedule |
| 1# | 10 | Vehicle (PBS) | — | sc | bid to end | — | — | — | — |
| 2 | 10 | SR1 | 0.4862 | sc | bid to end | — | — | — | — |
| 3 | 10 | SR1 | 4.86 | sc | bid to end | — | — | — | — |
| 4 | 10 | SR1 | 48.62 | sc | bid to end | — | — | — | — |
| 5 | 10 | Anti-PD-1-SCE | 33.33 | ip | biwk x 2 | — | — | — | — |
| 6 | 10 | Anti-PD-1-SCE | 100 | ip | biwk x 2 | — | — | — | — |
| 7 | 10 | SR1 | 0.4862 | sc | bid to end | Anti-PD-1-SCE | 33.33 | ip | biwk x 2 |
| 8 | 10 | SR1 | 4.86 | sc | bid to end | Anti-PD-1-SCE | 33.33 | ip | biwk x 2 |
| 9 | 10 | SR1 | 48.62 | sc | bid to end | Anti-PD-1-SCE | 33.33 | ip | biwk x 2 |
| 10 | 10 | SR1 | 0.4862 | sc | bid to end | Anti-PD-1-SCE | 100 | ip | biwk x 2 |
| 11 | 10 | SR1 | 4.86 | sc | bid to end | Anti-PD-1-SCE | 100 | ip | biwk x 2 |
| 12 | 10 | SR1 | 48.62 | sc | bid to end | Anti-PD-1-SCE | 100 | ip | biwk x 2 |
| 13 | 10 | Cyclophosphamide | 300* | ip | qd x 1 | — | — | — | — |
| 14 | 8 | LOOK SEE | — | iv | qd x 1 | — | — | — | — |

Control Group

*Mg/kg

TABLE 5B

Study II Result

| Group | n | Agent | Treatment Regimen μg/animal | Route | Schedule | Mean Met Count | SEM | n | Inhibition % | Statistical Significance vs G1 | vs G2 | vs G3 | vs G4 | vs G5 | vs G6 | Mean BW Nadir | Deaths TR | NTR |
|---|---|---|---|---|---|---|---|---|---|---|---|---|---|---|---|---|---|---|
| 1 | 10 | Vehicle | — | sc | bid to end | 160 | 16.2 | 10 | — | — | — | — | — | — | — | — | 0 | 0 |
| 2 | 10 | SR1 | 0.4862 | sc | bid to end | 186 | 12.6 | 10 | −17% | ns | — | — | — | — | — | — | | |
| 3 | 10 | SR1 | 4.86 | sc | bid to end | 182 | 22.9 | 10 | −14% | ns | — | — | — | — | — | — | 0 | 0 |
| 4 | 10 | SR1 | 48.62 | sc | bid to end | 167 | 27.1 | 10 | −5% | ns | — | — | — | — | — | — | 0 | 0 |
| 5 | 10 | Anti-PD-1-SCE | 33.33 | ip | biwk x 2 | 131 | 12.4 | 10 | 18% | ns | — | — | — | — | — | −0.9% Day 2 | 0 | 0 |
| 6 | 10 | Anti-PD-1-SCE | 100 | ip | biwk x 2 | 127 | 11.4 | 10 | 21% | ns | — | — | — | — | — | −0.9% Day 2 | 0 | 0 |
| 7 | 10 | SR1 Anti-PD-1-SCE | 0.4862 33.33 | sc ip | bid to end biwk x 2 | 102 | 15.4 | 10 | 36% | * | *** | — | — | ns | — | −1.4% Day 2 | 0 | 0 |
| 8 | 10 | SR1 Anti-PD-1-SCE | 4.86 33.33 | sc ip | bid to end biwk x 2 | 144 | 11.4 | 10 | 10% | ns | — | ns | — | ns | — | −1.5% Day 2 | 0 | 0 |
| 9 | 10 | SR1 Anti-PD-1-SCE | 48.62 33.33 | sc ip | bid to end biwk x 2 | 103 | 18.3 | 10 | 36% | ns | — | — | ns | ns | — | — | 0 | 0 |
| 10 | 10 | SR1 Anti-PD-1-SCE | 0.4862 100 | sc ip | bid to end biwk x 2 | 103 | 16.2 | 10 | 36% | ns | *** | — | — | — | ns | −1.0% Day 2 | 0 | 0 |
| 11 | 10 | SR1 Anti-PD-1-SCE | 4.86 100 | sc ip | bid to end biwk x 2 | 96 | 10.9 | 10 | 40% | * | — | ** | — | — | ns | — | 0 | 0 |
| 12 | 10 | SR1 Anti-PD-1-SCE | 48.62 100 | sc ip | bid to end biwk x 2 | 98 | 9.6 | 10 | 39% | * | — | — | * | — | ns | −0.8% Day 2 | 0 | 0 |
| 13 | 10 | Cyclophosphamide | 300* | ip | qd x 1 | 2 | 0.5 | 10 | 99% | *** | — | — | — | — | — | −8.0% Day 2 | 0 | 0 |

*mg/kg
Days in Progress = 15
n = number of animals in a group not dead from accidental causes (NTR deaths excluded from TGD calculations)
Percent Inhibition = [1 − (T/C)] × 100, compared to Group 1
Mean BW Nadir = lowest group mean body weight, as % change from Day 1;
— indicates no decrease in mean body weight was observed
TR = treatment-related death;
NTR = non-treatment-related death
Statistical Significance (Anova Dunnett's test for Group 1, 2, 5, 7; Group 1, 3, 5, 8; Group 1, 4, 5, 9; Group 1, 2, 6, 10; Group 1, 3, 6, 11; Kruskal-Wallis-Dunn test for Group 1, 4, 6, 12 or Unpaired t-test with Welch's correction for G1 vs. G13):
ns = not significant,
* = P < 0.05,
** = P < 0.01,
*** = P < 0.001,
compared to group indicated The result indicates that at certain doses the combination of ZDX (Ta1)+anti-PD-1 treated groups exhibited fewer metastases compared to groups treated with Ta1 or anti-PD-1 alone. Such result supports that thymosin treatment can provide positive statistically significant reduction in metastases in B16F10 murine lung metastases model, with efficacy trends in combination with an anti-PD-1 antibody.

The activity of 44 biomarkers in mice under each treatment was analyzed. Among these biomarkers, several biomarkers showed statistically significant differential activity between mice treated only with Ta1 or anti-PD-1 alone, and mice treated with a combination of Ta1 and anti-PD-1. Such biomarkers include, but are not limited to Apolipoprotein A-I, Leptin, Lymphotactin, Macrophage Colony-Stimulating Factor-1 (M-CSF-1), Monocyte Chemotactic Protein-5 (MCP-5), Stem Cell Factor (SCF), and Vascular Cell Adhesion Molecule-1 (VCAM-1).

Figure 8:
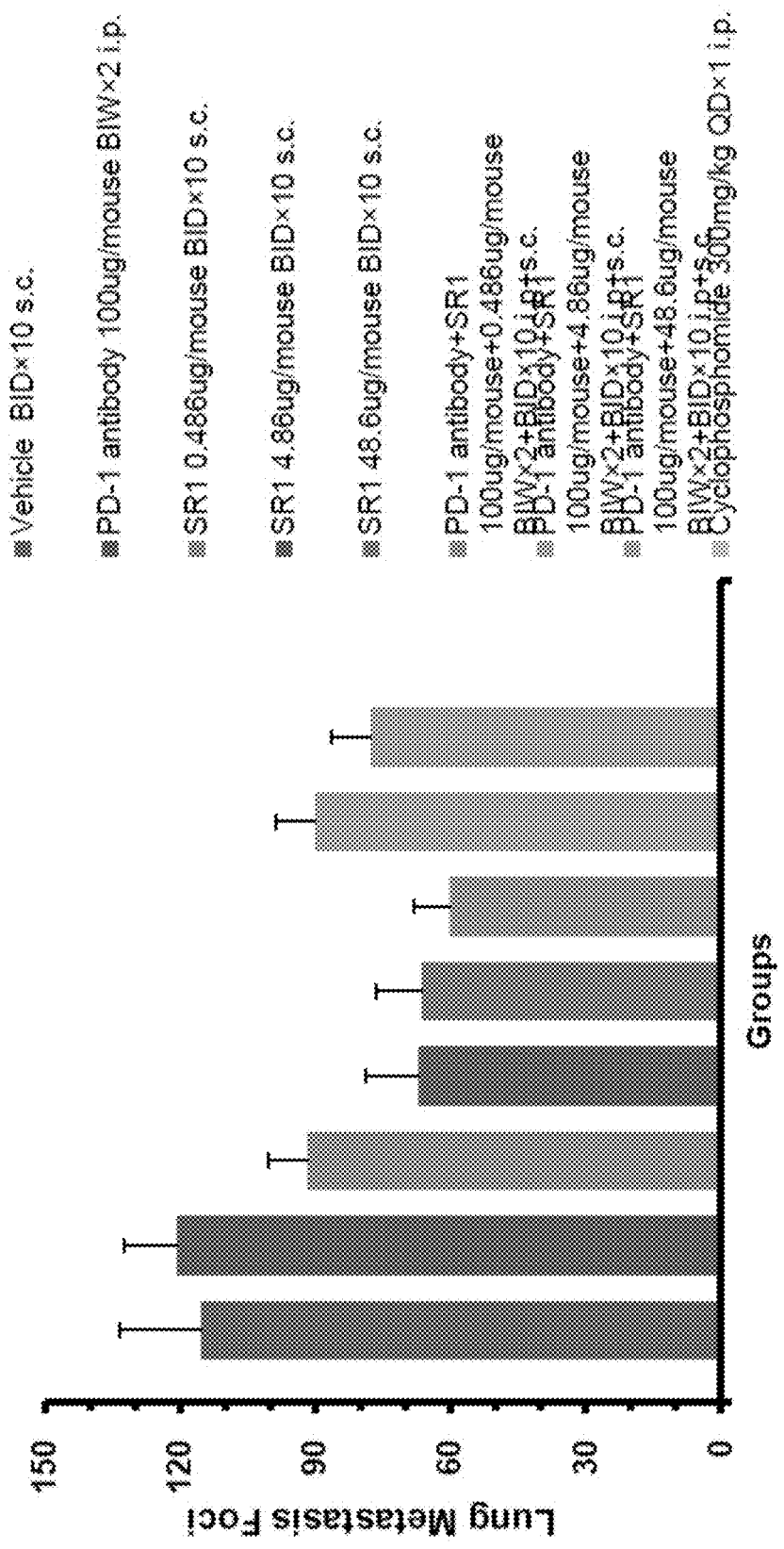
FIG. 8 depicts lung metastasis foci in the different groups at Day 13 post tumor inoculation treated with vehicle, thymosin alone, anti-PD-1 alone, thymosin plus anti-PD-1, or cyclophosphamide.

A similar study was performed in an independent laboratory to confirm the results. The result is shown in Table 6 and FIG. 8. Interestingly, in this study, the anti-PD-1 did not work as well as the study above, but the TA1 did. This can be attributed to lot differences in the anti-PD-1 antibody sourced by both labs and to the fact that B16F10 doesn't always respond to anti-PD-1 in lung met models. The important thing is that the combination of anti-PD-1 and TA1, especially at the low dose of TA1 showed a statistically significant decrease in lung mets and there were positive trends in the other two combination groups. Thus, these preliminary studies do confirm additive or possibly synergistic effects of the two in combination, especially when one of the two doesn't seem to work as single agent.

TABLE 6

Antitumor Activity of Thymalfasin as Single Agent and in Combination with PD-1 Antibody in the Treatment of Systemic B16F10 Murine Melanoma Model

| Group | Treatment | Number of metastasis foci on day 13 (Mean ± SEM) | Inhibition (%) | P value* |
|---|---|---|---|---|
| 1 | Vehicle | 115 ± 18 | — | — |
| 2 | PD-1 antibody (100 μg/mouse) | 121 ± 12 | −4.87 | 0.684 |
| 3 | TA1 (0.486 μg/mouse) | 92 ± 9 | 20.35 | 0.288 |
| 4 | TA1 (4.86 μg/mouse) | 67 ± 12 | 41.83 | 0.003 |
| 5 | TA1 (48.6 μg/mouse) | 66 ± 10 | 42.26 | 0.008 |
| 6 | PD-1 antibody (100 μg/mouse) + TA1 (0.486 μg/mouse) | 60 ± 8 | 47.83 | 0.002 |
| 7 | PD-1 antibody (100 μg/mouse) + TA1 (4.86 μg/mouse) | 90 ± 9 | 21.91 | 0.248 |

TABLE 6-continued

Antitumor Activity of Thymalfasin as Single Agent and in Combination with PD-1 Antibody in the Treatment of Systemic B16F10 Murine Melanoma Model

| Group | Treatment | Number of metastasis foci on day 13 (Mean ± SEM) | Inhibition (%) | P value* |
|---|---|---|---|---|
| 8 | PD-1 antibody (100 μg/mouse) + TA1 (48.6 μg/mouse) | 78 ± 9 | 32.61 | 0.06 |
| 9 | Cyclophosmide (300 mg/kg) | 0 ± 0 | 100 | <0.001 |

Unless defined otherwise, all technical and scientific terms herein have the same meaning as commonly understood by one of ordinary skill in the art to which this invention belongs. Although any methods and materials, similar or equivalent to those described herein, can be used in the practice or testing of the present invention, the preferred methods and materials are described herein. All publications, patents, and patent publications cited are incorporated by reference herein in their entirety for all purposes.

The publications discussed herein are provided solely for their disclosure prior to the filing date of the present application. Nothing herein is to be construed as an admission that the present invention is not entitled to antedate such publication by virtue of prior invention.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

What is claimed:

1. A method of treating cancer or a metastasis thereof in a subject comprising administering a composition comprising therapeutically effective amount of a first immune stimulator and a second immune stimulator, wherein the first immune stimulator is an alpha thymosin peptide, and the second immune stimulator is a programmed cell death-1 (PD-1) inhibitor.

2. The method of claim 1, wherein the subject is a human.

3. The method of claim 1, wherein the second immune stimulator is administered to said subject at a dosage of about 0.01-1000 mg/day.

4. The method of claim 1, wherein the alpha thymosin peptide is administered to the subject during at least a portion of the treatment at a dosage within a range of about 0.5-10 mg/day.

5. The method of claim 4, wherein said dosage of the alpha thymosin peptide is within a range of about 0.1-10 mg/day.

6. The method of claim 1, wherein the alpha thymosin peptide is thymosin alpha 1 (TA1).

7. The method of claim 6, comprising administration of TA1 daily for a period of about 1-10 days, followed by about 1-5 days of non-administration of TA1.

8. The method of claim 7, wherein TA1 is administered daily for about 3-5 days, followed by about 2-4 days of non-administration of TA1.

9. The method of claim 8, wherein TA1 is administered daily for about 4 days, followed by about 3 days non-administration of TA1.

10. The method of claim 1, wherein the combination further comprises a kinase inhibitor.

11. The method of claim 10, wherein said kinase inhibitor comprises sorafenib.

12. The method of claim 10, wherein said kinase inhibitor is administered to said patient at a dosage within a range of about 10-200 mg/day.

13. The method of claim 1, wherein the composition further comprises an antineoplastic heat shock apoptosis activator (HSAA).

14. The method of claim 13, wherein said HSAA comprises STA-4783 (elesclomol).

15. The method of claim 13, wherein said HSAA is administered to said patient at a dosage within a range of about 0.01-100 mg/kg/day.

16. The method of claim 1, wherein said combination further includes administration of an antibody against cytotoxic T lymphocyte-associated antigen 4 (CTLA4).

17. The method of claim 16, wherein said CTLA4 antibody comprises 9H10, MDC010, 1F4, BNI3, Q01, A01, M08, 1B8, WKH203, ab9984, ab13486, ipilimumab, ticilimumab or a combination thereof.

18. The method of claim 16, wherein said CTLA4 antibody is administered to said patient at a dosage within a range of about 0.001-50 mg/kg/day.

19. The method of claim 1, wherein said combination further includes administration of an alkylating antineoplastic agent (AlkAA).

20. The method of claim 19, wherein the alkylating antineoplastic agent (AlkAA) comprises dacarbazine (DTIC).

21. The method of claim 19, wherein the alkylating antineoplastic agent (AlkAA) is administered to said patient at a dosage within a range of about 700-1300 mg/kg/day.

22. The method of claim 1, wherein the method further comprising administering a chemotherapeutic agent to the subject.

23. The method of claim 22, wherein the chemotherapeutic agent is dacarbazine (DTIC) or cisplatin.

24. The method of claim 1, wherein the cancer is melanoma.

25. The method of claim 24, wherein the composition further comprises an additional anti-melanoma agent.

* * * * *